(12) United States Patent
Sreejayan et al.

(10) Patent No.: US 7,271,278 B2
(45) Date of Patent: Sep. 18, 2007

(54) APPLICATION OF CHROMIUM-AMINO ACID COMPLEXES IN THE TREATMENT OF DIABETES AND OTHER DISEASES

(75) Inventors: Nair Sreejayan, Laramie, WY (US); Jun Ren, Laramie, WY (US); Xiaoping Yang, Laramie, WY (US)

(73) Assignee: The University of Wyoming, Laramie, WY (US)

( * ) Notice: Subject to any disclaimer, the term of this patent is extended or adjusted under 35 U.S.C. 154(b) by 0 days.

(21) Appl. No.: 11/476,287

(22) Filed: Jun. 28, 2006

(65) Prior Publication Data

US 2007/0015826 A1   Jan. 18, 2007

Related U.S. Application Data

(60) Provisional application No. 60/694,543, filed on Jun. 28, 2005.

(51) Int. Cl.
*C07F 11/00* (2006.01)
*A61K 31/28* (2006.01)
(52) U.S. Cl. .................. 556/63; 514/505
(58) Field of Classification Search ............ 556/63; 514/505
See application file for complete search history.

(56) References Cited

U.S. PATENT DOCUMENTS 5,266,560 A * 11/1993 Furman et al. .............. 514/4
6,689,383 B1   2/2004 Anderson
7,022,351 B2   4/2006 Abdel-Monem
2004/0253327 A1  12/2004 Niazi

OTHER PUBLICATIONS

Hisaya Oki, Bulletin of the Chemical Society of japan, vol. 50, No. 3, pp. 680-684 (1977).*
Ebner et al., Inorganic Chemistry vol. 19, No. 5, pp. 1347-1351 (1980).*
Ohh, et al., "Effects of different forms of chromium supplements on serum glucose, insulin, and lipids in rats," J. Food Science and Nutrition, 9:342-5 (2004) ABS only.
Yang, et al., "A newly synthetic chromium complex-chromium (phenylalanine)3 improves insulin responsiveness . . . ," FEBS Letters, 579:1458-1464, (2005).

* cited by examiner

*Primary Examiner*—Porfirio Nazario-Gonzalez
(74) *Attorney, Agent, or Firm*—Robert C. Netter; Kathleen D. Rigaut; Dann, Dorfman, Herrell & Skillman

(57) ABSTRACT

Compositions comprising chromium (III) 1:3 complexes comprising amino acids and methods of use thereof are provided.

19 Claims, 15 Drawing Sheets

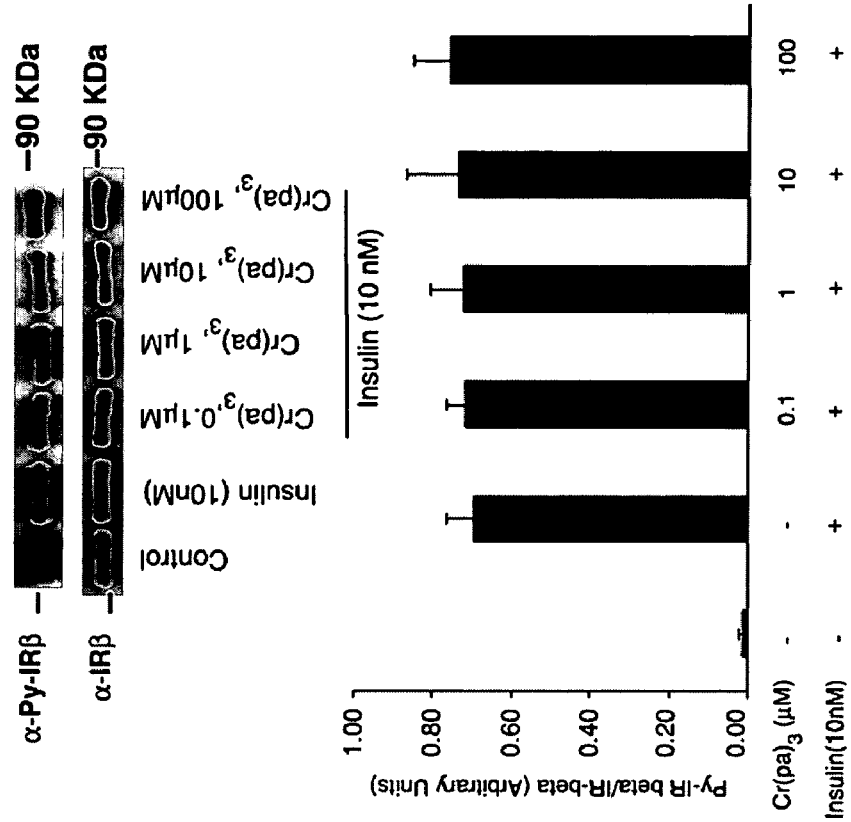
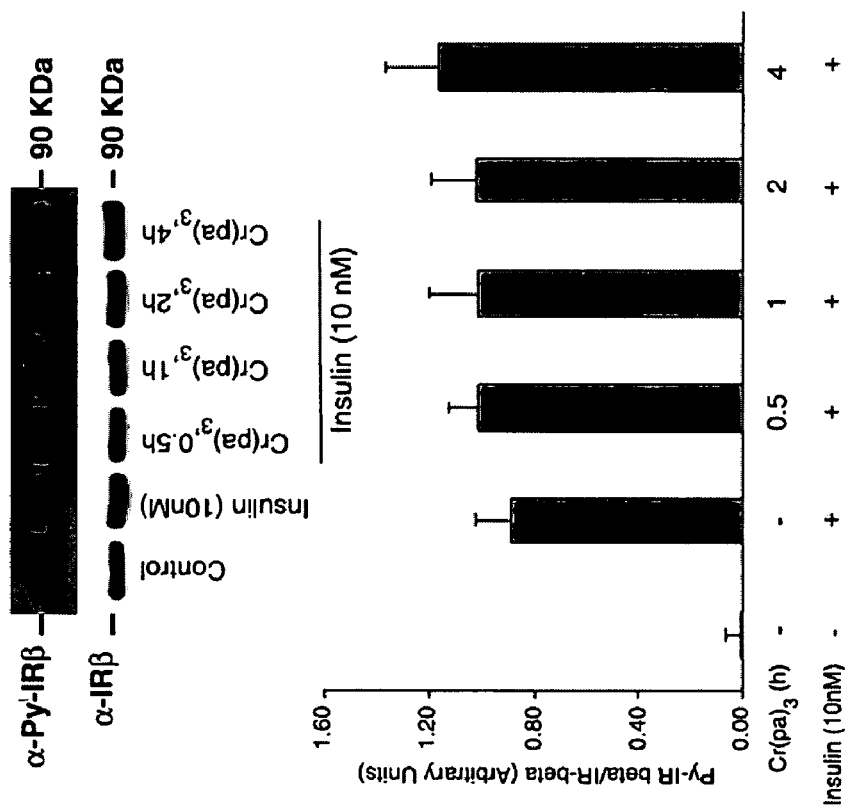

APPLICATION OF CHROMIUM-AMINO ACID COMPLEXES IN THE TREATMENT OF DIABETES AND OTHER DISEASES

This application claims priority under 35 U.S.C. §119(e) to U.S. Provisional Patent Application No. 60/694,543, filed on Jun. 28, 2005. The foregoing application is incorporated by reference herein.

Pursuant to 35 U.S.C. Section 202(c), it is acknowledged that the United States Government has certain rights in the invention described herein, which was made in part with funds from the National Institutes of Health Grant No. P20 RR015553.

FIELD OF THE INVENTION

The present invention relates to chromium(III) complexes coordinated with amino acids and methods of use thereof.

BACKGROUND OF THE INVENTION

Insulin resistance is concomitant with type II diabetes, obesity, hypertension, and other features of the metabolic syndrome (DeFronzo (2004) Med. Clin. North. Am., 88:787-835). It is the major risk factor for cardiovascular diseases and one of the leading causes of mortality and morbidity. Proper management of insulin resistance has been shown to play a pivotal role in the reduced risk for cardiovascular diseases. However, compounds which improve the sensitivity of insulin are somewhat limited. Compounds such as pioglitazone augment the action of insulin by increasing insulin sensitivity and may be of benefit for the long-term treatment for type II diabetes. The mineral chromium is thought to play a key role in normal carbohydrate metabolism by potentiating the action of insulin, leading to increased insulin sensitivity in type II diabetes and obesity (Anderson (2000) Diabetes Metab., 26:22-27). Dietary deficiency of chromium has been shown to increase the risk of developing diabetes (Jeejeebhoy et al. (1977) Am. J. Clin. Nutr., 30:531-538). Clinical trials have demonstrated that supplementation with chromium chloride or chromium picolinate can lower blood glucose levels in diabetic patients (Morris et al. (2000) Diabet. Med., 17:684-685).

Better bioavailability of low-molecular-weight organic chromium complexes as compared to chromium salts (2-5% versus 0.5-2%) has led to the development of low-molecular-weight organic complexes of chromium as therapeutic agents to counter the diminished insulin effect under type II diabetes (Vincent (2004) Proc. Nutr. Soc., 63:41-47). Emerging evidence has shown that the biologically active form of chromium is a chromium-oligopeptide complex, which further justifies the use of organic-chromium-complexes as biomimetic chromium supplements (Yamamoto et al. (1987) Eur. J. Biochem., 165:627-631). U.S. Pat. No. 6,149,948 also demonstrates the ability of chromium containing complexes to decrease plasma cholesterol and triglycerides (see also Clodfelder et al. (2005) J. Biol. Inorg. Chem. 10:119-130; Cefalu et al. (2002) J. Nutr. 132: 1107-1114). The chromium complex of picolinic acid, one of the most popularly used dietary supplements has been shown to modulate intracellular pathways of glucose metabolism and improve comorbidities associated with insulin resistance in several animal and human studies (Anderson et al. (1997) Diabetes, 46:1786-1791; Lee and Reasner (1994) Diabetes Care, 17:1449-1452). However, recent reports have indicated that the picolinate ligand may shift the redox potential of chromium in the complex such that it can be reduced by biological reductants to generate hydroxyl radicals causing deleterious DNA mutations (Stearns et al. (1995) FASEB J., 9:1643-1648; Bagchi et al. (2002) Toxicology, 180:5-22). This pro-oxidant nature of chromium picolinate may greatly limited its therapeutic applications.

SUMMARY OF THE INVENTION

In accordance with one aspect of the instant invention, chromium (III) complexes comprising amino acids are provided. The chromium (III) may be complexed with L-, D-, or D,L-amino acids. In a particular embodiment, amino acids are D- or D,L-amino acids. Preferred amino acids include phenylalanine, isoleucine, proline, cysteine, and methionine. In a preferred embodiment, the amino acid is phenylalanine, more preferably D-phenylalanine. In one embodiment, the chromium (III) complex has the formula:

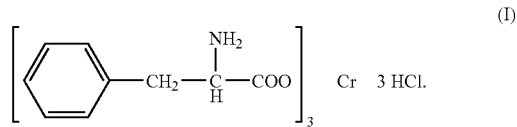

In accordance with another aspect of the instant invention, compositions comprising chromium (III) complexed with amino acids and a pharmaceutically acceptable carrier are provided. Optionally, the compositions may further comprise at least one other agent useful for treating diabetes.

Methods for forming chromium (III) complexes comprising amino acids, particularly D-amino acids such as D-phenylalanine, are provided. Exemplary methods comprise heating a mixture of a chromium (III) salt with three molar equivalents of the amino acid.

In yet another aspect of the instant invention, methods for the treatment and/or prevention of diabetes, and/or insulin resistance syndrome in a patient in need thereof are provided. The methods comprise administering an effective amount of the compositions of the instant invention.

In yet another embodiment, the compositions of the instant invention can be administered to a patient in need thereof to decrease plasma cholesterol and/or triglycerides.

BRIEF DESCRIPTIONS OF THE DRAWING

FIG. 1 is a graphic representation of mouse 3T3-adipocytes treated with insulin (6 nM) in the presence or absence of $Cr(pa)_3$ (5 or 25 µM) for 10 days accompanying the procedure of differentiation of the cells. Results are mean±standard error of measurement (SEM). * $P<0.05$, n=3.

FIGS. 2A and 2C are Western blots of lysates of 3T3-adipocytes pretreated with $Cr(pa)_3$ (5 µM) for different times (FIG. 2A) or at different concentrations for 2 hours (FIG. 2C) followed by stimulation with 10 nM of insulin for 10 minutes. The blots are probed with phospho-IGF-IR (Tyr1131)/Insulin receptor (Tyr1146) antibody (upper panels) and reprobed with antibody against insulin receptor beta (lower panels). FIGS. 2B and 2D are graphical representations of the respective optical densities of the phosphorylated bands to that of the total protein of the blots of FIGS. 2A and 2C. Values are means±SEM, n=3 or 4.

FIGS. 3A and 3C are Western blots of lysates of 3T3-adipocytes pretreated with $Cr(pa)_3$ (5 µM) for different times (FIG. 3A) or at different concentrations for 2 hours (FIG. 3C) followed by stimulation with 10 nM of insulin for 10 minutes. The blots are probed with a phospho-Akt (thr308) antibody and reprobed with Akt antibody. FIGS. 3B and 3D are graphical representations of the respective optical densities of the phosphorylated bands to that of the total protein of the blots of FIGS. 3A and 3C. Values are means±SEM, n=3. * P<0.05 compared to insulin treatment in the absence of Cr(pa)$_3$.

FIG. 4A is a graphical representation of the intraperitoneal glucose tolerance test (IPGTT) in ob/ob (+/+) mice and lean controls before and after a 6-week treatment with Cr(pa)$_3$ (150 μg/kg/day). Values are means±SEM, * P<0.005 (n=10), vs. vehicle-treated ob/ob (+/+) mice. FIG. 4B is a graphical representation of the area under the plasma glucose concentration curve (AUC) following IPGTT for obese and lean mice treated with Cr(pa)$_3$ or control. * P<0.005.

FIG. 5A is a graphical representation of the assay for generation of hydroxyl radicals for basal reaction mixture containing the test compounds Cr(pa)$_3$ or chromium picolinate (1.2 μM). Ferric-EDTA (100 μM) was used as a positive control. FIG. 5B is an image of a gel showing the effects of chromium picolinate and Cr(pa)$_3$ on ascorbate-stimulated cleavage of pUC19 DNA.

FIG. 6A is a blot of phosphorylated Akt and total Atk in 3T3-adipocytes under various treatments. FIG. 6B is a graphical representation of the ratios of the gel optical densities of phosphorylated Akt versus total protein. Values are means±SEM, n=3. * P<0.05.

Figure 9:
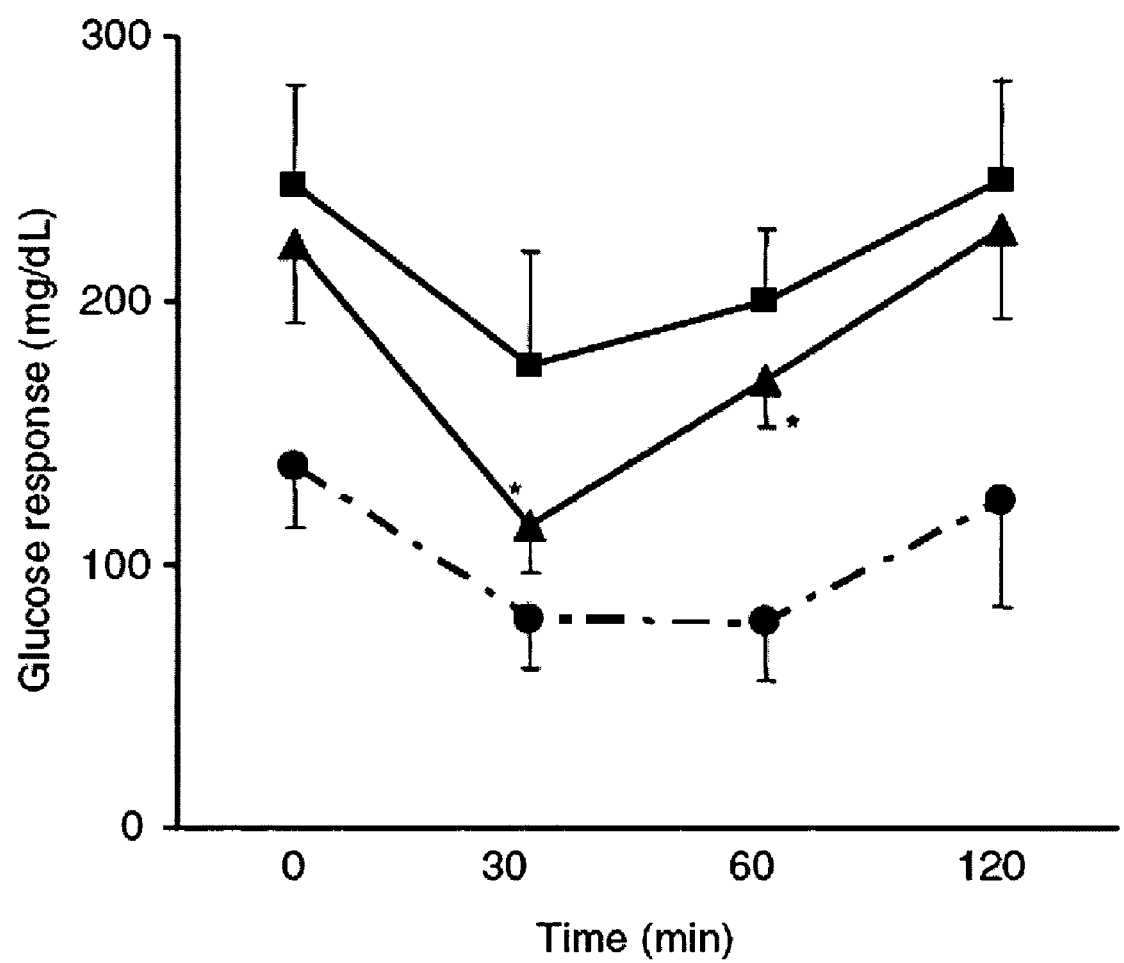

FIG. 9 is a graphical representation of the effect of Cr(D-Phe)$_3$-treatment on insulin-sensitivity in obese mice. Following oral treatment with Cr(pa)$_3$ (150 μg/kg/day for 6 weeks) mice were challenged with an intraperitoneal injection of insulin (1 U/kg body weight). Blood glucose levels were estimated prior to (0 minute) and at various time following insulin challenge. Cr(D-Phe)$_3$-treated obese group (closed triangle) had a significantly lower glucose level compared to obese control animals (closed square). Closed circle indicated glucose level of lean control group. Values are means±SEM, * p<0.005, n=12 versus vehicle-treated ob/ob(+/+) mice, at indicated time points.

Figure 10:
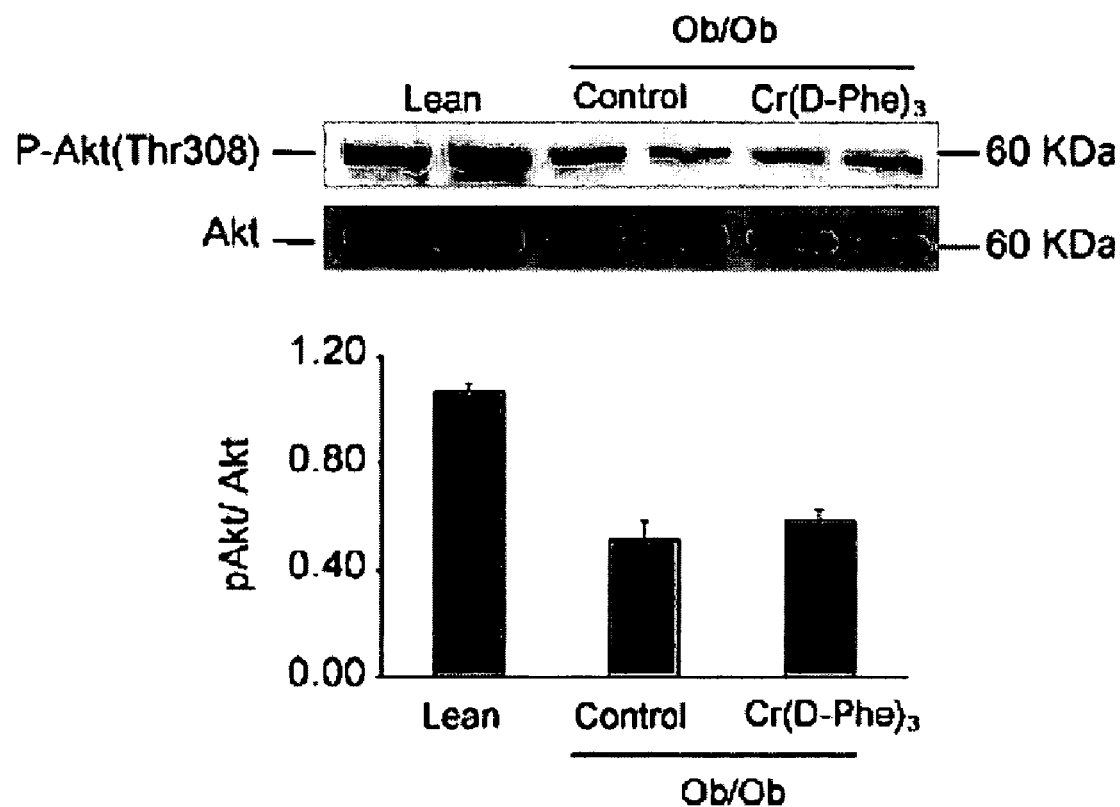

FIG. 10 demonstrates the effect of Cr(D-Phe)$_3$-treatment on hepatic Akt-phosphorylation. Following treatment with Cr(D-Phe)$_3$-treatment, the animals were sacrificed. The liver was isolated and liver homogenates were subjected to Western blotting against anti-phospho-Akt (upper panel) and reprobed with total Akt (lower panel). The bar graph represents the ratio of the optical densities of the phosphorylated protein versus total protein. Values are means±SEM, n=3. Obese mice had significantly lower levels (* p<0.05) of phospho-Akt compared to lean controls. Treatment with Cr(D-Phe)$_3$ failed to alter the levels of phospho-Akt.

Figure 11:
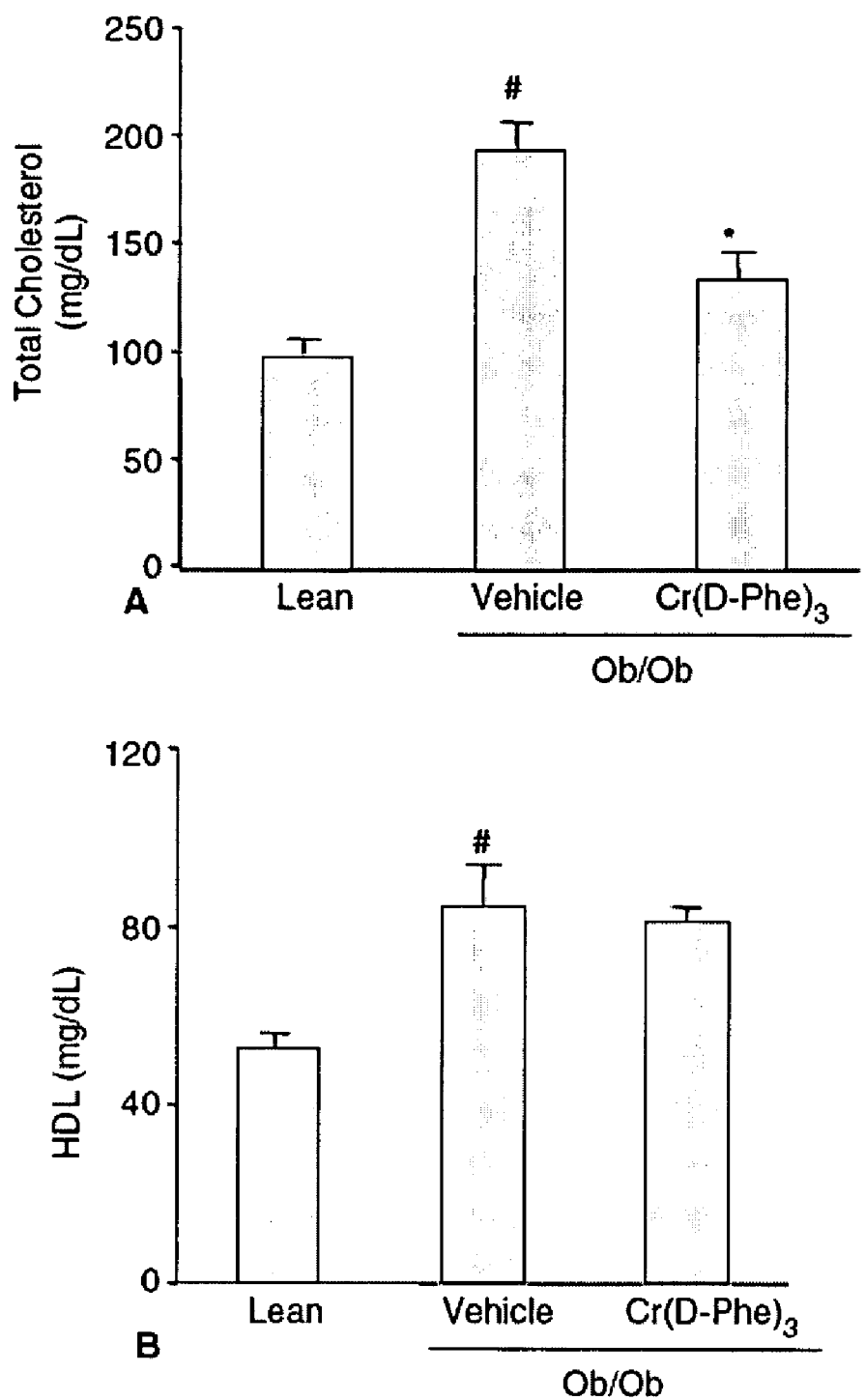

FIGS. 11A-11B are graphical representations of the effect of Cr(D-Phe)$_3$-treatment on serum lipids in obese mice. Animals were treated with Cr(D-Phe)$_3$ (150 μg/kg/day for 6 weeks). Serum was collected by centrifuging blood taken from hearts immediately after sacrificing the animals and plasma lipids were analyzed using a kit from Equal Diagnostics as per the protocol supplied by the manufacturer. FIG. 11A shows that serum cholesterol levels are significantly (# p<0.05) elevated in obese mice compared to lean control which is significantly attenuated (* p<0.05) by Cr(D-Phe)$_3$-treatment. FIG. 11B shows that serum HDL levels are elevated in obese mice compared to lean mice, which is not attenuated by Cr(D-Phe)$_3$. Values are means±SEM, n=6.

Figure 12:
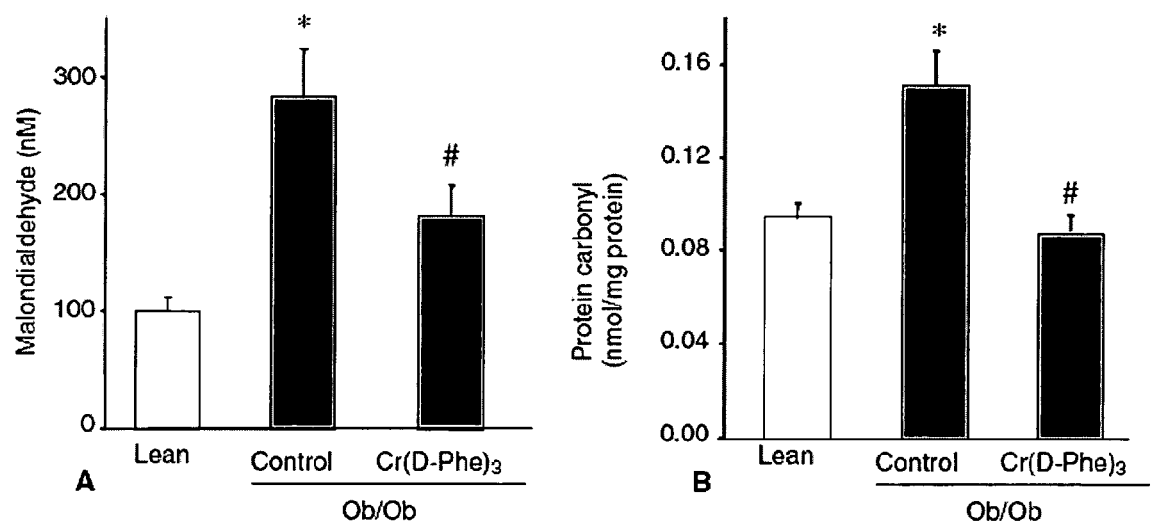

FIGS. 12A and 12B are graphical representations of the effect of Cr(pa)$_3$-treatment on lipid-peroxidation and protein carbonyl formation in liver homogenate. Following treatment of animals with Cr(pa)$_3$ (150 μg/kg/day for 6 weeks), livers were isolated, homogenized and the extent of lipid-peroxidation was assessed as malondialdehyde equivalents (FIG. 12A) and the protein carbonyl was estimated spectrophotometrically by measuring the absorbance of the carbonyl compound. Values are means±SEM, n=3. The levels of both these oxidant stress markers were significantly increased (* p<0.01) in the liver homogenate of obese animals compared to lean controls. Cr(D-Phe)$_3$-treated obese mice had significantly lower (# p<0.01) malondialdehyde and protein carbonyl formation. Results are mean±SEM of three independent experiments.

Figure 13:
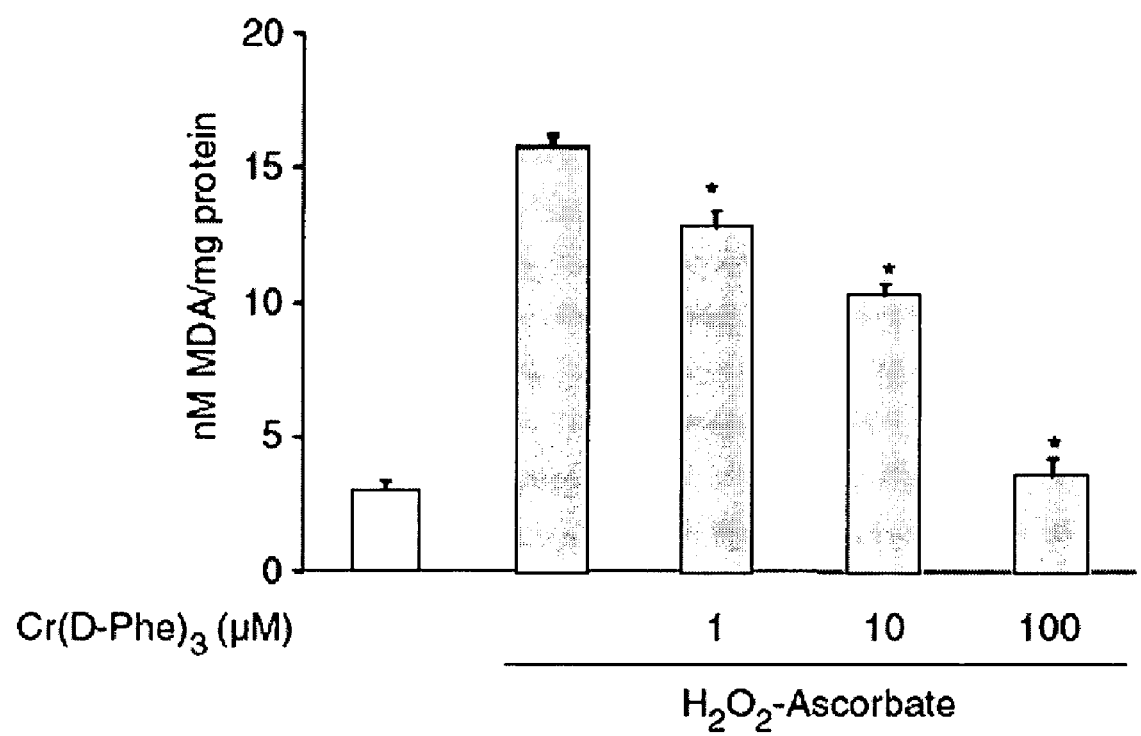

FIG. 13 is a graphical representation of the effect of in vitro lipid-peroxidation. Lipid-peroxidation of rat brain homogenate (10% w/v) was stimulated by hydrogen peroxide (1 mM) and ascorbate (1 mM) in the presence or absence of Cr(D-Phe)$_3$ for 30 minutes at 30° C. and extent of lipid-peroxidation was assessed as malondialdehyde equivalents. Values are means±SEM, n=3. * p<0.01 compared to control samples not treated with Cr(D-Phe)$_3$.

Figure 14:
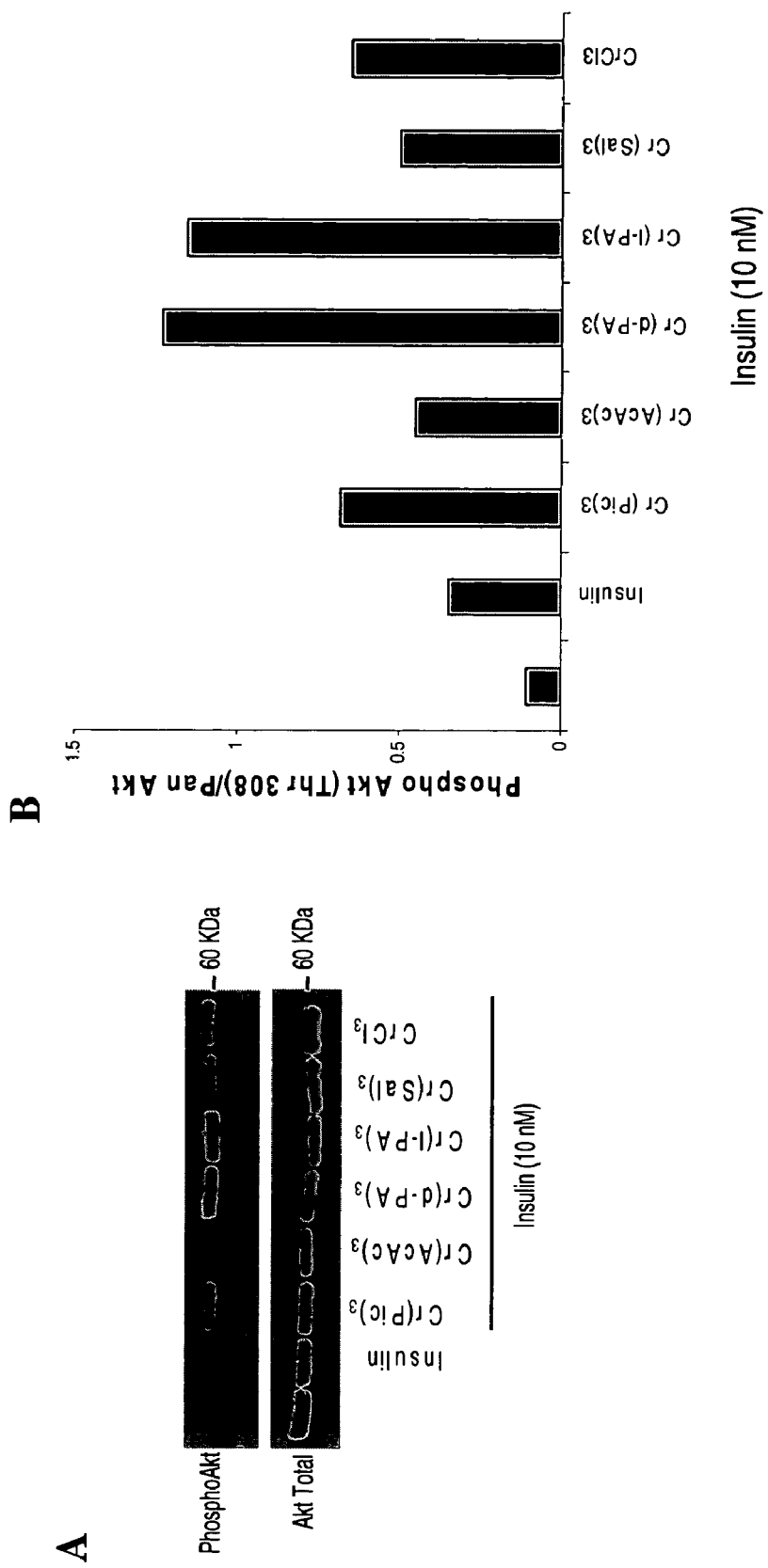

FIG. 14A contains images of Western blots of lysates of 3T3-adipocytes pretreated with various chromium containing complexes followed by stimulation with 10 nM of insulin. The blots are probed with a phospho-Akt (thr308) antibody and reprobed with Akt antibody. FIG. 14B is graphical representations of the respective optical densities of the phosphorylated bands to that of the total protein of the blots of FIG. 14A.

DETAILED DESCRIPTION OF THE INVENTION

The instant invention provides complexes of chromium with amino acids. In one embodiment, chromium (III) is complexed with D-amino acids. In particular, the amino acids have antioxidant properties such as, without limitation, phenylalanine, proline, isoleucine, cysteine, and methionine. The chromium may be complexed to three of the same amino acid or with different amino acids. In one embodiment, the amino acid complexed with chromium (III) is D-phenylalanine. The chromium may also be complexed to amino acid derivatives (e.g., phenylalanine comprising inorganic and/or organic substituents of the phenyl ring) and analogs. The chromium (III) complexes of the instant invention include salts thereof. While the instant specification exemplifies the specific use of chromium (III) D-phenylalanine (Cr(pa)$_3$ or Cr(D-Phe)$_3$), the instant invention can be performed with any chromium (III) complex comprising amino acids.

Herein, it is demonstrated that (i) Cr(pa)$_3$ enhances insulin-stimulated glucose uptake in adipocytes, (ii) Cr(pa)$_3$ improves insulin-signal transduction in cultured mice adipocytes, (iii) feeding of Cr(pa)$_3$ to insulin resistant animals improves glucose tolerance, and (iv) Cr(pa)$_3$ does not generate toxic hydroxyl radicals that cleave DNA under physiological conditions. Indeed, the instant invention is the first demonstration that a synthetic complex of chromium with D-phenylalanine improves insulin responsiveness and whole body glucose tolerance. Unlike chromium picolinate, Cr(pa)$_3$ does not result in the production of harmful metabolic by-products which cleave DNA under physiological conditions. Taken together, chromium complexes of amino acids, particularly D-amino acids such as D-phenylalanine, comprise a novel class of chromium complexes which are less toxic and beneficial for the treatment and management of insulin resistance and glucose intolerance in type II diabetes.

The ability of chromium to enhance insulin-stimulated glucose uptake in cultured cells has been reported previously (Yoshimoto et al. (1992) Metabolism, 41:636-642). Though the exact mode of action of chromium is unknown, several mechanisms have been proposed. Chromium is thought to increase insulin binding to cells, to enhance the insulin receptor number and to potentiate insulin receptor kinase activity (Davis and Vincent (1997) Biochemistry, 36:4382-4385). As described herein, however, $Cr(pa)_3$ does not increase the protein levels of insulin receptor nor does it enhance the tyrosine phosphorylation of insulin receptor indicating that chromium may be acting downstream of the insulin receptor. Phosphorylation of Akt in response to insulin stimulation is a pivotal event in insulin signal transduction that results in the activation and translocation of glucose transporter GLUT4-containing vesicles from the cytosol to plasma membrane leading to cellular glucose uptake (Wang et al. (1999) Mol. Cell Biol., 19:4008-4018). Besides its involvement in the activation of GLUT4 vesicles, Akt can phosphorylate glycogen synthase kinase 3, which is an essential step in the activation of glycogen synthase, the enzyme involved in glycogen synthesis. While not being bound to any particular theory, $Cr(pa)_3$ may be improving insulin sensitivity by enhancing insulin-stimulated phosphorylation of Akt. Interestingly, a recently conducted clinical study demonstrates that individuals with type-II diabetes who supplemented their diet with chromium picolinate had increased activity of Akt in their skeletal muscles compared to those who were on placebo (Cefalu et al. (2003) Chromium picolinate supplementation increases insulin-stimulated Akt phosphorylation in vivo in skeletal muscle from subjects with type 2 diabetes. 18th International Diabetes Federation Congress, Abstract). The reported ability of wortmanin, a PI3-kinase inhibitor to inhibit Cr-stimulated potentiation of insulin activity (Anderson, R. A. (1998) J. Am. Coll. Nutr., 17:548-555) underscores Akt as a potential target for chromium compounds. Furthermore, the results presented here (see, e.g., FIG. 6) suggest that $Cr(pa)_3$ may function as a more potent enhancer of insulin-stimulated Akt phosphorylation than chromium picolinate. However, the mechanism by which chromium enhances insulin-stimulated Akt phosphorylation is presently unclear. One potential explanation could be the inhibition of the enzyme phosphotyrosine phosphatase (PTP-1B) by chromium, which is a known negative regulator of insulin signaling (Goldstein et al. (2001) J. Trace Elem. Exp. Med., 14:393-401).

The discovery that chromium in its biologically active form complexes with a 1500 Da polypeptide led to the synthesis and evaluation of several low-molecular-weight organic chromium complexes amongst which chromium picolinate has been the most extensively studied compound (Vincent, J. B. (2000) Acc. Chem. Res., 33:503-510). One problem with chromium picolinate is its poor solubility in physiological buffers thereby resulting in poor bioavailability. Besides, the picolinate ligand has been shown to generate hydroxyl radicals that can cause deleterious DNA damage (Bagchi et al. (2002) Toxicology, 180:5-22; Speetjens et al. (1999) Chem. Res. Toxicol., 12:483-487). These observations emphasize the need for non-toxic ligands to chelate chromium.

Phenylalanine, besides having better solubility at physiological pH, is a known scavenger of hydroxyl radicals (Nukuna et al. (2001) J. Am. Chem. Soc., 123:1208-1214). U.S. Patent Application Publication 2003/0228394 describes the use of L-amino acid chromium complexes for the use in animal feed. In the instant invention, however, the chromium complexes comprise D-, L-, or D,L-amino acids. Notably, D-amino acids possess increased biological half-lives, are potentially less immunogenic than their L-amino acid counterpart, and may not result in the complications associated with phenylketonuria as seen with L-isomers. In a particular embodiment, the chromium complexes comprise D-phenylalanine. Notably, derivatives of D-phenylalanine, such as nateglinide, have also shown to have beneficial effects in type II diabetes (Phillips and Dunning (2003) Int. J. Clin. Pract., 57:535-541). As demonstrated herein, the D-phenylalanine complex of chromium is less toxic, is a more effective biomimetic complex of chromium, and has superior insulin-potentiating properties.

Chromium (III) (Cr(III)) is the most stable state of chromium and has a coordination number of six. The hexacoordinated trivalent chromium forms relatively kinetically inert octahedral complexes. The novel Cr(III) complexes coordinated with amino acids, particularly D-phenylalanine, of the instant invention are represented by the exemplary structure in FIG. 8 and other salts thereof.

The complexes of the instant invention may be prepared as described in Example 1. More generally, a chromium salt (e.g., $CrCl_3$) is heated in an aqueous solution with 3 molar equivalents of the desired amino acid(s), such as D-phenylalanine. The mixture is heated to at least about 70° C., more preferably to about 80° C. Heating with reflux typically occurs for about 1 to 10 hours, more preferably for about 4 hours. The mixture can then be dried (e.g., freeze-dried) to obtain the solid of the desired product.

In accordance with one aspect of the instant invention, $Cr(pa)_3$ can be administered to animals, including humans, that are in need of chromium. Individuals in need of chromium include, for example, those not obtaining enough in their diet, those exhibiting insulin resistance or impaired glucose tolerance, and those suffering from diabetes (particularly type II diabetes). Compositions comprising $Cr(pa)_3$ can be administered to patients to treat and/or prevent, without limitation, diabetes, hyperglycemia, hyperlipidemia, obesity, and insulin resistance syndrome. Compositions comprising $Cr(pa)_3$ can also be administered to patients as a preventive measure against diabetes in those individuals with pre-diabetes, insulin resistance, or impaired glucose tolerance.

Additionally, compositions comprising $Cr(pa)_3$ can also be administered to patients to decrease plasma cholesterol and/or triglycerides. Such compositions may further comprise at least one other agent capable of reducing levels of plasma cholesterol and/or triglycerides (see, e.g., U.S. Pat. No. 6,149,948).

Compositions of the instant invention comprise chromium-amino acid complexes in an amount sufficient to produce the desired effect. In a particular embodiment, the compositions comprise from about 10 μg to about 1500 μg.

The compositions may also further comprise other agents for treating diabetes. As used herein, the term "agents for treating diabetes" includes agents that are effective at treating, preventing, and/or managing insulin resistance, diabetes, and diabetes precursor syndromes. Examples of agents for treating diabetes include, without limitation, vanadium containing compounds (e.g., vanadyl sulfate), magnesium containing compounds (e.g., magnesium chloride), biguanides (e.g., metformin, Glucophage, and Glucophage XR), thiazolidinediones (e.g., troglitazone, rosiglitazone, Actos, and Avandia), sulfonylureas (e.g., tolbutamide, glyburide, glipizide, Dymelor, Diabinese, Orinase, Tolinase, Glucotrol, Glucotrol XL, DiaBeta, Micronase, Glynase PresTab and Amaryl), benzoic acid derivatives (e.g. repaglinide), and α-glucosidase inhibitors (e.g. acarbose, miglitol, Precose, and Glyset) (see, e.g., U.S. Pat. Nos. 5,962,030 and 6,376,549 and U.S. Patent Application Publications 2003/0078269 and 2004/0034030).

The compositions of the instant invention may also further comprise at least one pharmaceutically acceptable carrier suitable for mode of delivery. The term "pharmaceutically acceptable carrier" includes any and all solvents, dispersion media and the like which may be appropriate for the desired route of administration of the pharmaceutical composition. The instant compositions may be administered, for example, orally (e.g., in food or in pill (e.g., capsule, tablet, and lozenge, optionally time-released) form), rectally, or parenterally (e.g., intravenously and intramuscularly). The compositions may be used in the form of a solid, a powder, a solution, a syrup, an emulsion, a dispersion, a micelle, a liposome, or any other form suitable for use. Suitable pharmaceutically acceptable carriers and formulations are described in Remington's Pharmaceutical Sciences, 19th Ed. (Mack Publishing Co., Easton, 1995). Common carriers include, without limitation, water, oil, buffered saline, ethanol, polyol (for example, glycerol, propylene glycol, liquid polyethylene glycol and the like), dimethyl sulfoxide (DMSO), detergents, suspending agents, glucose, lactose, gum acacia, gelatin, mannitol, starch paste, magnesium trisilicate, talc, corn starch, keratin, colloidal silica, potato starch, urea, medium chain length triglycerides, dextrans, other carriers suitable for use in manufacturing preparations, in solid, semisolid, or liquid form, and suitable mixtures thereof. In addition excipients and auxiliary, stabilizing, preserving, thickening, flavoring, and coloring agents may be included in the compositions.

The following examples describe illustrative methods of practicing the instant invention and are not intended to limit the scope of the invention in any way.

EXAMPLE 1

Insulin receptor beta polyclonal antibody was obtained from Santa Cruz Biotechnology (Santa Cruz, Calif.). All other antibodies used in this example were from Cell Signaling Technology Inc (Beverly, Mass.). Dulbecco's Modified Eagle Medium (DMEM), penicillin-streptomycin liquid, insulin/transferrin/selenous acid (ITS), fetal bovine serum (FBS), newborn calf serum (CS) were from Invitrogen Corporation (Carlsbad, Calif.). Micro BCA protein assay kit was from Pierce Chemical (Rockford, Ill.). pUC19 DNA was obtained from New England Biolabs (Beverly, Mass.). Chromium picolinate was a kind gift from Dr. J. B. Vincent (The University of Alabama, Tuscaloosa, Ala.). All other chemicals were from Sigma-Aldrich Chemical Co (St. Louis, Mo.). Doubly deionized water was used to prepare stock solutions of chromium complex for all experiments unless otherwise indicated.

To synthesize $Cr(pa)_3$, aqueous solutions of $CrCl_3 \cdot 6H_2O$ (2.6 g; 10 mmol in 50 ml water) and D-phenylalanine (4.8 g, 30 mmol in 50 ml water) were mixed at 80° C. and refluxed for 4 hours. The homogeneous green reaction mixture was freeze-dried. The greenish-violet solid obtained was washed with acetone and dried in air oven. Yield: 81%, m.p. >300° C. Found: C, 47.84; H, 5.60; N, 5.92. The stoichiometry $Cr(C_{27}H_{30}N_3O_6) \cdot 3HCl \cdot 2H_2O$ requires C, 47.00; H, 5.40; N, 6.09. The ESMS of the complex in methanolic solution registers signals at 545.1 and 165.9 representing, respectively, the tris chelate and the deprotonated ligand. Formation of the complex was associated with $v_{C=O}$ (1563 cm$^{-1}$) and $v_{N-H}$ (3535 cm$^{-1}$) shifts in the IR-spectrum by about 40 and 30 cm$^{-1}$, respectively. The broadening of the moderately sharp absorption band in the free ligand (2900-3100 cm$^{-1}$) to about 600 cm$^{-1}$ may be attributed to the reorganization in intramolecular hydrogen bonding after chelation. New absorption bands in the far IR region around 370 and 310 cm$^{-1}$ can be assigned to the Cr—O and Cr—N bonds. The UV-Vis spectrum of the methanolic solution of the complex registered bands at 15673 cm$^{-1}$ ($v_1$) and 22075 cm$^{-1}$ ($v_2$). The complex being green in color, the above two bands are due to the absorption in yellow and blue parts of the spectrum. These absorptions are due to the spin allowed transitions $^4T_{2g} \leftarrow {}^4A_{2g}$ ($v_1$) and $^4T_{1g}(F) \leftarrow {}^4A_{2g}$ ($v_2$). The third band $v_3$ overlaps with UV absorption of the ligand. These observations suggest a hexa-coordinate environment around chromium (III). The pH of the aqueous solution of the complex is 4.7 and the presence of chloride demonstrates the presence of HCl in the lattice. Based on the stoichiometry, elemental analysis and spectral studies, the product obtained is a complex containing a 1:3 ratio of chromium to phenylalanine.

The 3T3-L1-pre-adipocytes were obtained from the American Type Culture Collection and were propagated at 37° C. in DMEM with 10% newborn calf serum plus 50 U/ml penicillin and 50 μg/ml streptomycin in an incubator under a humidified atmosphere of 5% $CO_2$/95% air. Induction of differentiation was done one day post-confluence. Cells were maintained in differentiation medium of the following composition: DMEM, 10% FBS, 0.2 1 g/ml dexamethasone, 0.5 mM 1-isobutyl-3-methylxanthine (IBMX) and ITS for three days. At day 3, the dexamethasone and IBMX were removed with ITS remaining on the cells for an additional two days. Differentiation was allowed to continue in DMEM supplemented with 10% FBS, ITS and the adipocytes were used between day 9 and 14 post-induction. Prior to the cellular assays, cells were serum starved by overnight incubation in DMEM (containing 0.2% serum).

Cells were lysed in RIPA buffer (150 mM NaCl, 0.25% sodium desoxycholate, 1% NP-40, 1 mM EDTA and 50 mM Tris, pH 7.2) containing 2 mM sodium vanadate, 1 μM PMSF, 1 μM sodium fluoride, 1 μg/ml aprotinin, 1 μg/ml leupeptin, and 1 μM pepstatin and sonicated to reduce the sample viscosity. The lysate was centrifuged at 15000×g for 15 minutes at 4° C. and the protein concentration in the supernatant was determined by the bicinchoninic acid method. Equivalent amounts of proteins were boiled in Laemmli sample buffer. Proteins 10-20 μg were separated on 7.5-10% polyacrylamide gel, and electrophoretically transferred to a nitrocellulose membrane. The membranes were incubated for 1 hour at room temperature in blocking buffer (5% w/v non-fat dry milk in tris buffered saline containing 0.1% Tween 20). Membranes were incubated in appropriate phospho-specific primary antibody for insulin receptor beta or Akt at 1:2500 dilutions in the blocking buffer followed by incubation with horseradish peroxidase-coupled secondary antibodies with appropriate specificity. Immunoreactive bands were visualized using enhanced chemiluminescence reagents (Cell Signaling Technology, Inc, Beverly, Mass.). Blots were then stripped and re-probed with antibodies directed against insulin receptor β and Akt.

All animal treatment procedures described in this example were approved by the animal Care and Use Committee at University of Wyoming (Laramie, Wyo.). Homozygous B6.V-lep ob>/J male mice purchased from the Jackson Laboratory (Bar Harbor, Me.) at age 5 weeks were divided randomly into two weight-matched groups, marked as ob/ob (+/+) control and ob/ob(+/+) treatment (n=10). Number, age and weight matched normal C57 mice were used as lean control. All of these animals were maintained on conventional laboratory diet under well-controlled conditions of temperature (22±2° C.), humidity (55±5%) and 12 hour/12 hour light-dark cycle and had ad libitum access to water and standard rodent chow. Rodent diet and tap water were consumed by mice ad libitum. $Cr(pa)_3$ was provided in the drinking water and, on the basis of water intake, was administered to provide an intake of about 150 µg/kg/day corresponding to about 10-15 µg elemental Cr/kg/day for ob/ob(+/+) and lean treatment groups. The dosage of chromium used was based on earlier animal studies reported with chromium picolinate (Cefalu et al. (2002) J. Nutr., 132:1107-1114).

At the end of the treatment schedule, mice were subjected to the intraperitoneal glucose tolerance test (IPGTT) as described previously (Hintz et al. (2003) Int. J. Obes. Relat. Metab. Disord., 27:1196-1203). Briefly, the mice were fasted for 12 hours and then given intraperitoneal injection of glucose (2 g/kg body weight). Glucose levels were determined in blood drops obtained by clipping the tail of the mice immediately before glucose challenge, as well as at 15, 60 and 120 minutes thereafter. Serum glucose levels were determined using ACCU-CHEK® Advantage® Glucose Analyzer (Roche Diagnostics Corporation, Ind.). Results of IPGTT are also expressed as integrated areas under the curves (AUC) over 120 minutes for glucose calculated by using the WinNonlin software (Pharsight Corporation, Mountain View, Calif.).

The potential of chromium compounds to generate hydroxyl radicals in vitro was assessed by the method reported previously (Halliwell et al. (1987) Anal. Biochem., 165:215-219). Briefly, a reaction mixture containing either chromium picolinate or $Cr(pa)_3$, 2-deoxyribose (4 mM), ascorbic acid (100 µM) and hydrogen peroxide (100 µM) in potassium phosphate buffer (pH 7.4, 10 mM) was incubated at 37° C. for 30 minutes. An aliquot of the mixture was treated with 1% (w/v) thiobarbituric acid and 2.8% (w/v) trichloroacetic acid and heated at 90° C. for 10 minutes, rapidly cooled and the amount of chromogen formed in the sample was measured by its absorption at 532 nm. Ferric-EDTA (100 µM) was used as a positive control.

DNA cleavage-stimulated by chromium compounds was assessed as described previously (Speetjens et al. (1999) Chem. Res. Toxicol., 12:483-487). All solutions were prepared using Chelex-100 treated water to remove any traces of metal ions. Aliquots of pUC19 (about 40 µM in base pairs in 5 mM Tris, 500 µM EDTA buffer, pH 8.0) were mixed with ascorbic acid (5 mM) in the presence of the test compounds in phosphate buffered saline (pH 7.4), to give a final volume of 15 µl. Reactions were allowed to proceed 60 minutes at room temperature followed by quenching with 2 µl of nucleic acid sample loading buffer. The mixtures were loaded directly onto a 1% agarose gel pre-stained by ethidium bromide and electrophoresed at 60 V. The gels were photographed on a UV transilluminator.

Glucose uptake activity was analyzed by measuring the uptake of 2-deoxy-D-[$^3$H] glucose as described previously (Sakoda et al. (1999) Diabetes, 48:1365-1371). Briefly, confluent 3T3-L1 adipocytes grown in 6-well plates were washed twice with serum-free DMEM and incubated with 2 ml of the same medium at 37° C. for 2 hours. The cells were washed 3 times with Krebs-Ringer-HEPES (KRH) buffer and incubated with 2 ml KRH buffer at 37° C. for 30 minutes. Insulin (6 nM) and/or $Cr(pa)_3$ (0-25 µM) were then added to adipocytes accompanying the procedure of differentiation. Glucose uptake was initiated by the addition of 0.1 ml KRH buffer and 2-deoxy-D-[$^3$H] glucose (0.2 µCi/ml) and 5 mM glucose as final concentrations. Glucose uptake was terminated by washing the cells three times with cold PBS. The cells were lysed overnight with 1 ml 0.5M NaOH and 0.1% SDS (w/v). The radioactivity retained by the cell lysates was determined by a scintillation counter (Beckmann LC 6000IC) and normalized to protein amount measured with a Micro BCA Protein Assay Kit (Pierce Chemical, Rockford, Ill.).

Data are expressed as means±S.E.M. and statistically evaluated using Student's paired t test using Sigma Plot statistical software (Jandel Scientific, San Rafael, Calif.). A P value of less than 0.05 was considered to be statistically significant.

A multi-step synthesis of chromium complexes of L-phenylalanine and D,L-phenylalanine using aqua(isothiocyanato)bis-(L-phenylalaninato)chromium and D,L- or L-phenylalanine as starting material has been reported previously (Oki et al. (1989) Synth. React. Inorg. Met.-Org. Chem., 19:1085-1091). In contrast, a simpler, single step reaction was used in this example to synthesize the complex of chromium(III) with D-phenylalanine in aqueous solution. The synthetic protocol used herein was closer to that reported by Abdel-Monem et al. (U.S. Patent Application Publication 20030228394) for the synthesis of similar complexes of chromium with L-amino acids. Elemental analysis and spectral studies indicate that the ratio of chromium to D-phenylalanine in the complex is 1:3.

Figure 1:
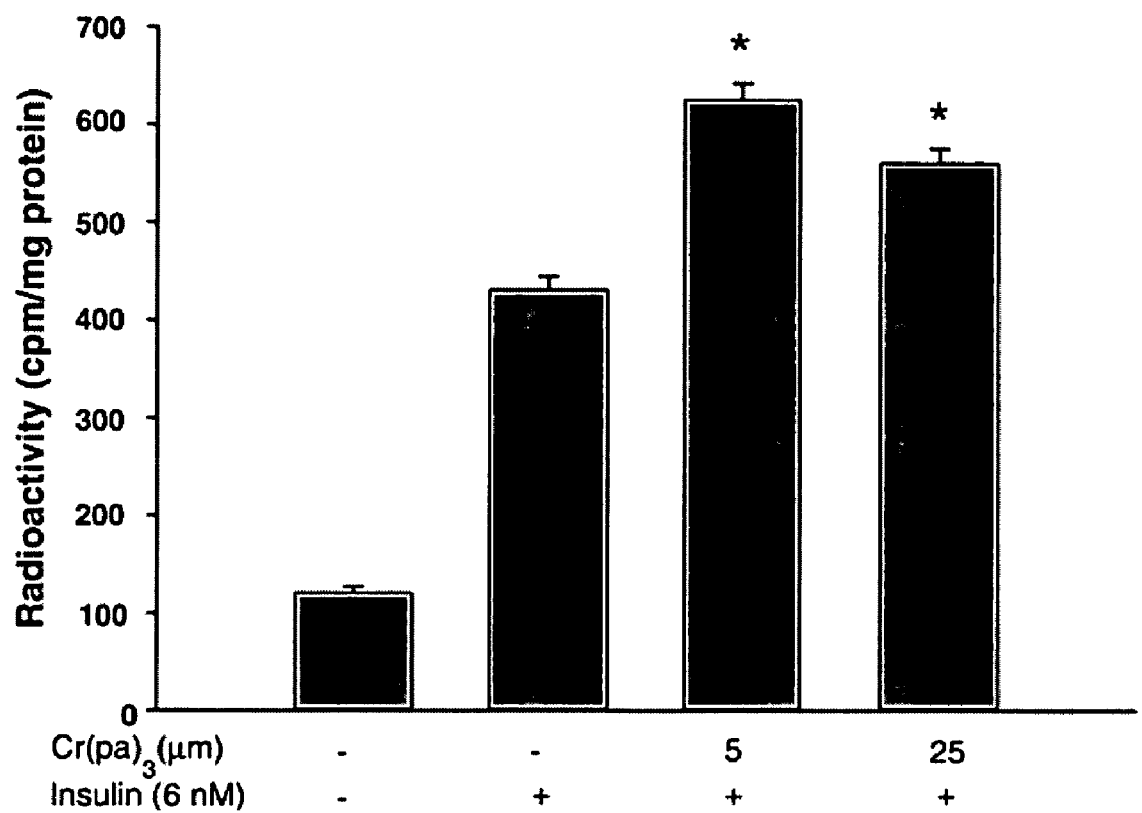

Chromium has been shown to improve insulin-stimulated glucose uptake in cultured cells sensitive to insulin (Yoshimoto et al. (1992) Metabolism, 41:636-642). The effect of $Cr(pa)_3$ on insulin-stimulated glucose-uptake in 3T3-adipocytes, an insulin-sensitive cell line, was investigated using the 2-deoxy-D-glucose-3H uptake assay. As shown in FIG. 1, incubation with insulin (6 nM) during the course of differentiation of the adipocytes, stimulated a fourfold increase in glucose uptake by adipocytes, consistent with a previous report (Sakoda et al. (1999) Diabetes, 48:1365-1371). Pre-incubation of the cells with $Cr(pa)_3$ (5 and 25 µM) significantly augmented insulin-stimulated glucose uptake in 3T3-adipocytes as compared to insulin-stimulated glucose uptake in untreated cells. In the absence of insulin, $Cr(pa)_3$ did not have any effect on basal glucose uptake. These results demonstrate that $Cr(pa)_3$ potentiates insulin-stimulated but not basal glucose uptake.

Insulin is thought to initiate its signaling cascade via activation and autophosphorylation of IRβ (Whitehead et al. (2000) Curr. Opin. Cell. Biol., 12:222-228). Once phosphorylated, the insulin receptor functions as a kinase which phosphorylates proteins such as the insulin receptor substrate (IRS) resulting in the downstream propagation of insulin signal. Since previous studies have shown that chromium complexes may enhance the number (Yoshimoto et al. (1992) Metabolism, 41:636-642) and activity (Davis and Vincent (1997) Biochemistry, 36:4382-4385) of the insulin receptors, subsequent experiments were performed to study the effect of $Cr(pa)_3$ on insulin-stimulated IRβ tyrosine phosphorylation in 3T3-adipocytes. Treatment with insulin resulted in a significant increase in phosphorylation of IRβ as expected, which was not altered by pretreating the cells with Cr(pa)$_3$ for various time or at different concentrations (FIGS. 2A and C). IRβ phosphorylation induced by submaximal concentrations of insulin (1 nM) was also not altered by Cr(pa)$_3$ indicating that receptor saturation by the ligand may not be the reason for the lack of effect of Cr(pa)$_3$. These results indicated that Cr(pa)$_3$ may enhance insulin-stimulated glucose-uptake via a mechanism(s) involving sites other than the insulin receptor.

Figure 3A:
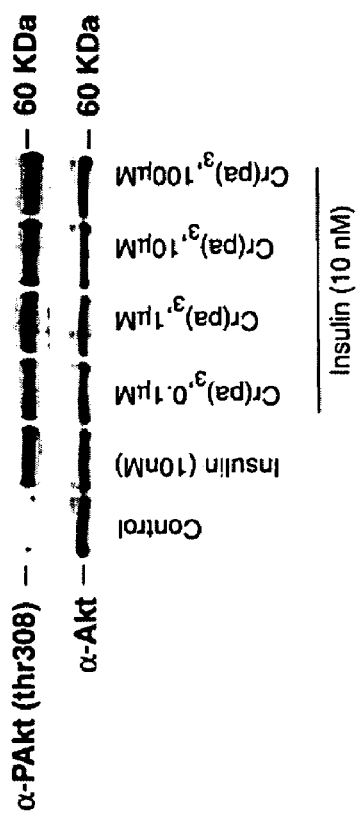
Figure 3C:
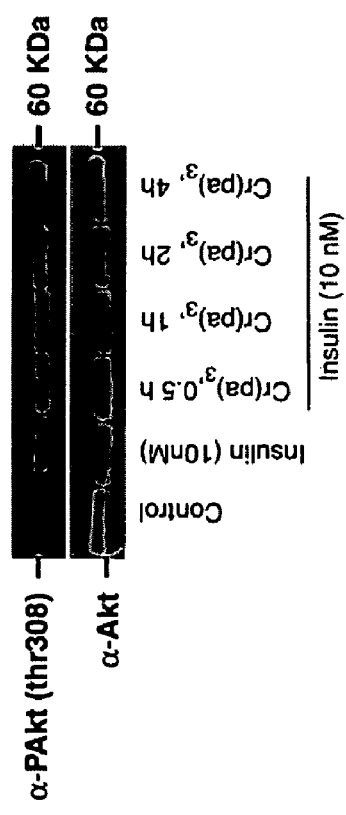
Figure 3B:
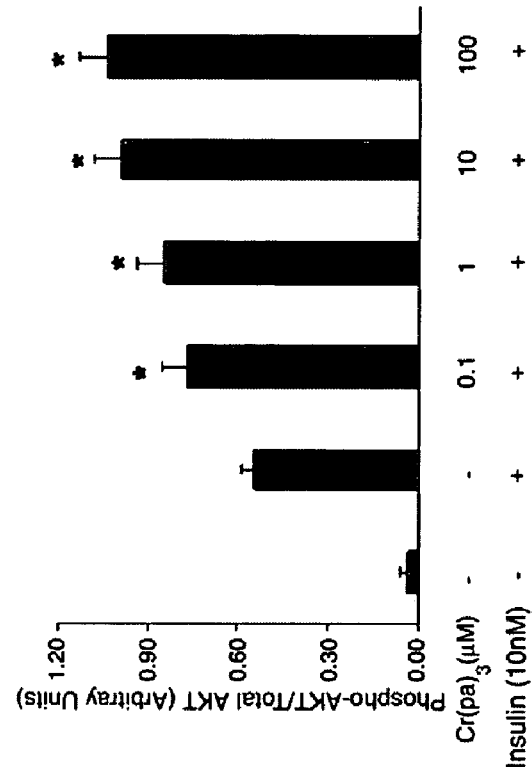
Figure 3D:
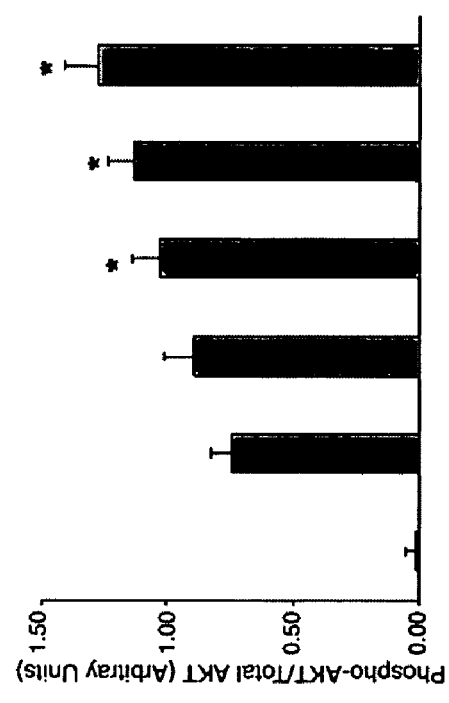

Akt has been identified as an important kinase, downstream of insulin receptor necessary for insulin activity (Katome et al. (2003) J. Biol. Chem., 278:28312-28323). Treatment of adipocytes with insulin resulted in an increase in Akt (thr308) phosphorylation (FIG. 3). Pretreatment of adipocytes with the chromium complex resulted in a further increase in the insulin-stimulated Akt phosphorylation both in a concentration-dependent (FIG. 3A, upper panel) and time-dependent manner (FIG. 3C, upper panel). Cr(pa)$_3$ alone, in the absence of insulin, did not alter the phosphorylation levels of Akt. These results indicate that Cr(pa)$_3$ may promote insulin signaling and glucose uptake by acting at the post-receptor level.

Figure 4:
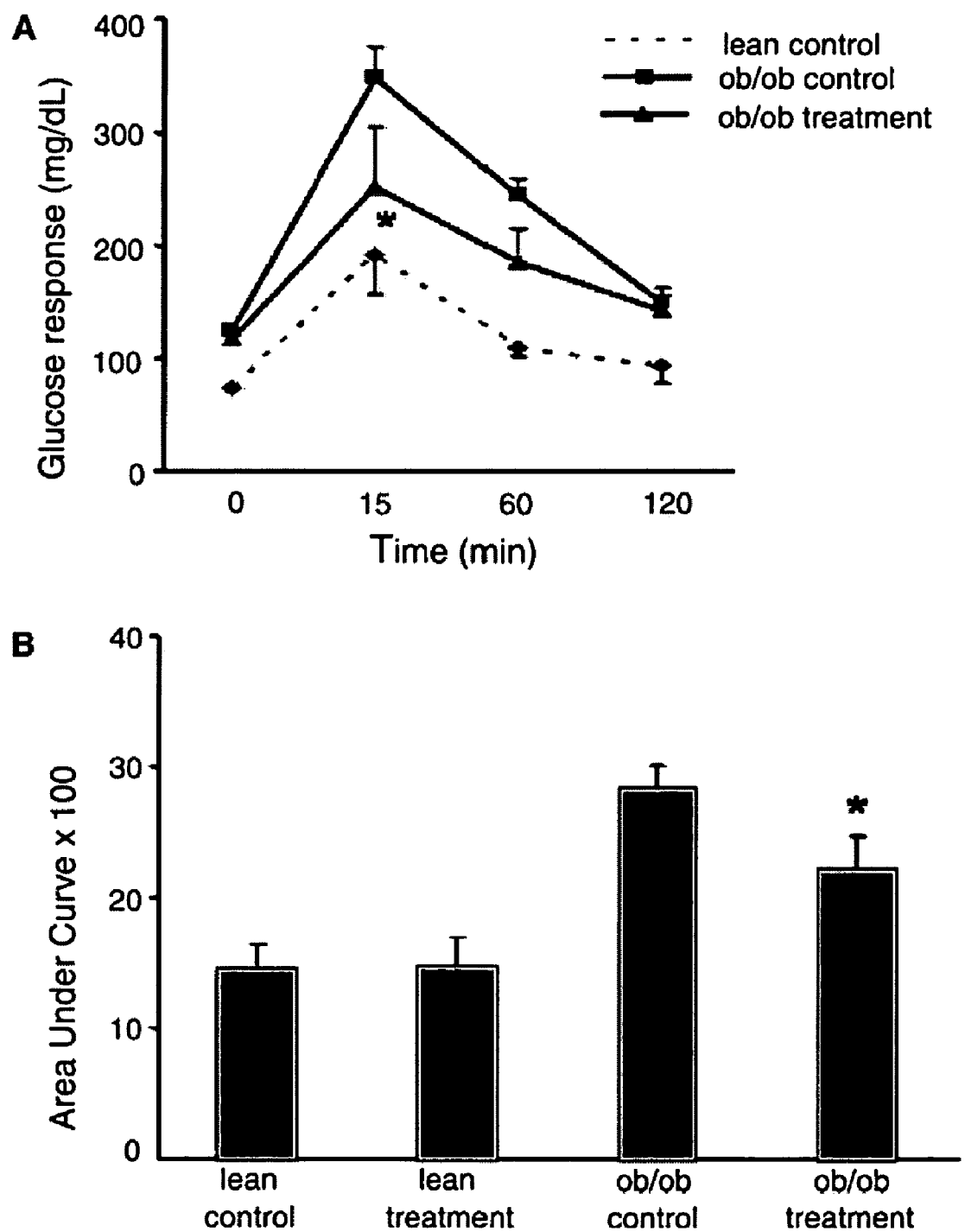

Genetically obese, leptin deficient C57BL/6J ob/ob(+/+) mice and their lean controls were treated with Cr(pa)$_3$ 150 μg/kg/d, for 6 weeks. Following acute glucose challenge, the ob/ob(+/+) animals showed poor glucose tolerance compared to the lean control mice as indicated by an increase in the area under the post-treatment glucose concentration curve (FIGS. 4A and B). In both Cr(pa)$_3$-treated and untreated animals, the plasma glucose levels following glucose challenge started to decline after peaking at 15 minutes and returned to the baseline value after 120 minutes (FIG. 4A). However, serum glucose levels in the Cr(pa)$_3$ treated ob/ob(+/+) mice were significantly lower than that of the untreated control animals at 15 and 60 minutes post-glucose-challenge (FIG. 4A). The integrated AUC over 120 minutes of glucose, shown in FIG. 4B, shows that the ob/ob(+/+) mice receiving Cr(pa)$_3$ have significantly lower AUC as compared to untreated animals. These effects of Cr(pa)$_3$ were found to be independent of the changes in the body weight as there was no significant difference in the body weight of the ob/ob(+/+) animals treated with Cr(pa)$_3$. Post-treatment weights were 52.2±1.6 g for treated versus 53.8±2.6 g for untreated (P>0.05 between the two groups, n=10). Pre-treatment weights were 28.2±1.1 and 28.8±1.0 g for treated and untreated group, respectively. In contrast, in the lean mice, there were no significant changes in the AUC between the Cr(pa)$_3$-treated and untreated group.

Figure 5:
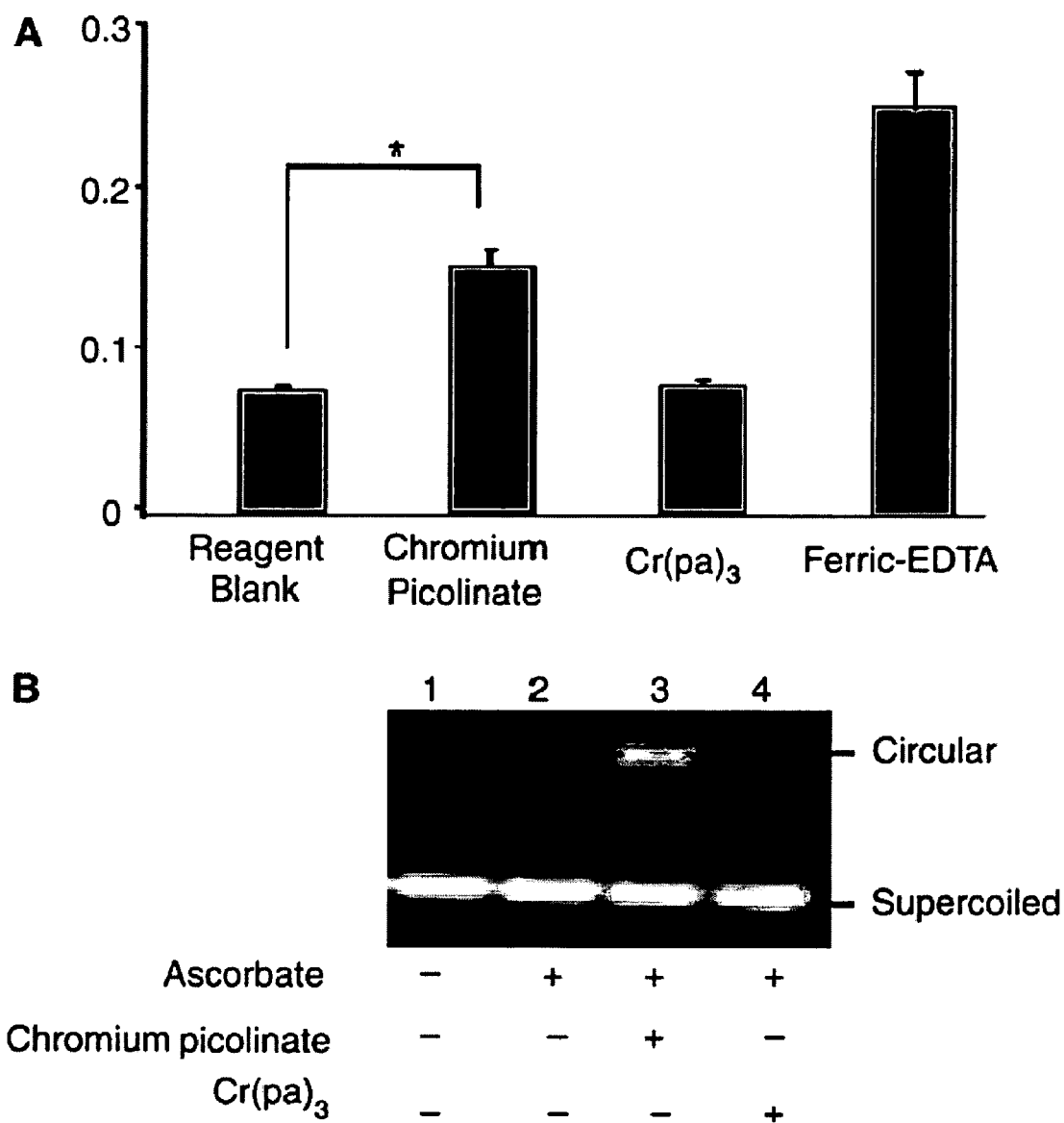

Recent studies have indicated that the nutritional supplement chromium picolinate can cause DNA damage by generating hydroxyl radicals (Speetjens et al. (1999) Chem. Res. Toxicol., 12:483-487). The mutagenic potential of chromium picolinate has been attributed by the picolinate ligand, which primes the redox potential of the chromic center for reduction by biological reductants (Hepburn and Vincent (2002) Chem. Res. Toxicol., 15:93-100). In contrast, the phenylalanine ligand is known to scavenge hydroxyl radicals via hydroxylation of the phenyl ring (Nukuna et al. (2001) J. Am. Chem. Soc., 123:1208-1214) which may be a potential strategy to avert the toxicity. The deoxyribose degradation assay was used to compare the pro-oxidant potential of chromium picolinate and Cr(pa)$_3$. Ferric-EDTA complex in the presence of ascorbate generated hydroxyl radicals causing significant damage to deoxyribose (FIG. 5A). In this model system, chromium picolinate induced a twofold increase (over control) in hydroxyl radical production. Ferric-EDTA generated hydroxyl radicals about 3.5 fold over the reagent blank. In contrast, Cr(pa)$_3$ failed to cause any degradation of deoxyribose, suggesting that this compound does not generate hydroxyl radicals under the conditions tested. The effect of Cr(pa)$_3$ on DNA damage was monitored by observing the conversion of the supercoiled plasmid DNA to circular, nicked form (FIG. 5B). In accordance with previous studies, chromium picolinate (1.2 μM), in the presence of ascorbic acid, caused a nick in the pUC19 DNA (38 μM) as seen by the conversion of supercoiled, faster migrating DNA to circular slower migrating DNA. Significantly, equimolar concentrations of Cr(pa)$_3$ under similar conditions failed to induce any strand breaks in the DNA.

Figure 6:
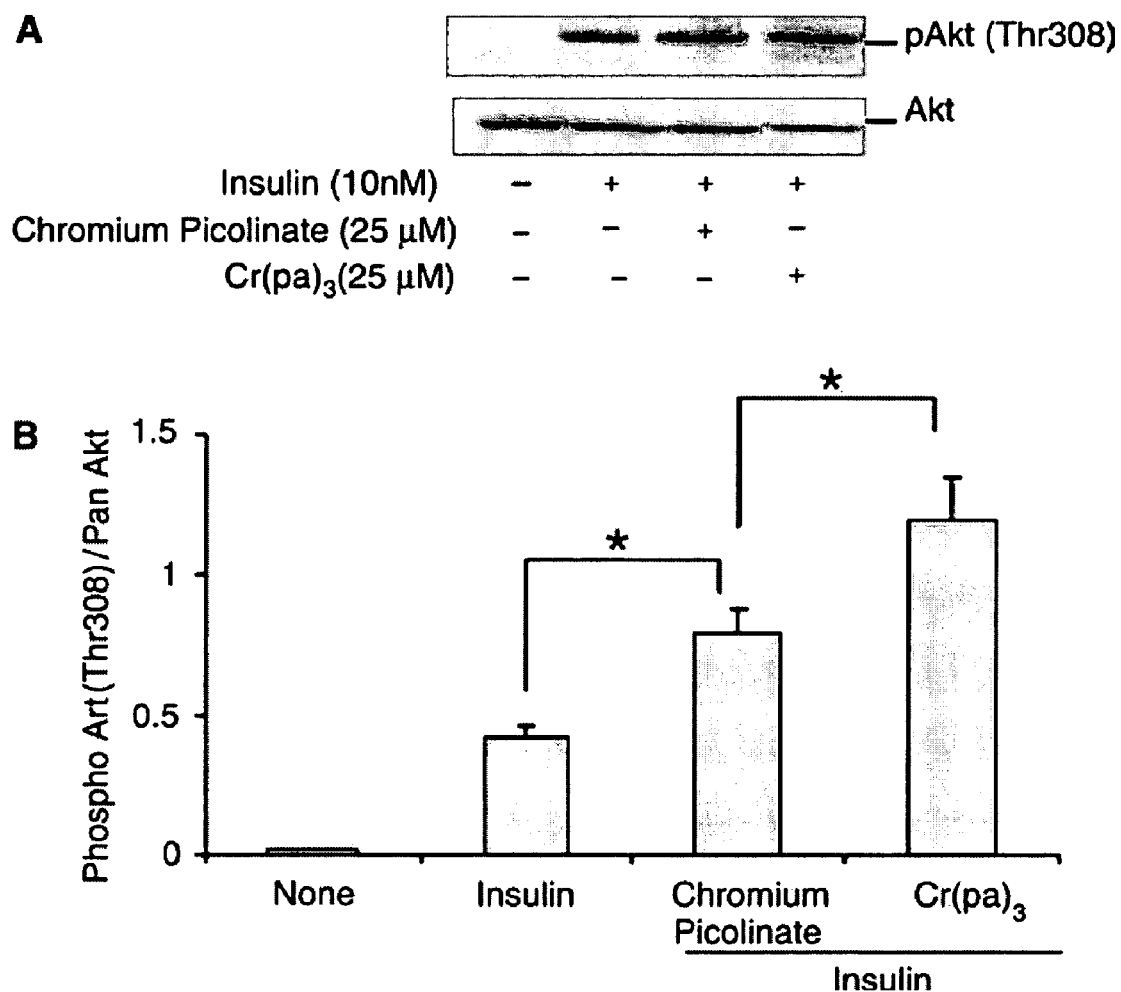

Insulin-stimulated phosphorylation of Akt is enhanced to a greater extent by Cr(pa)$_3$ as compared to that with chromium picolinate. FIG. 6 shows that Cr(pa)$_3$ induces greater stimulation of insulin-stimulated Akt phosphorylation as compared to chromium picolinate at equimolar concentrations.

Figure 7A:
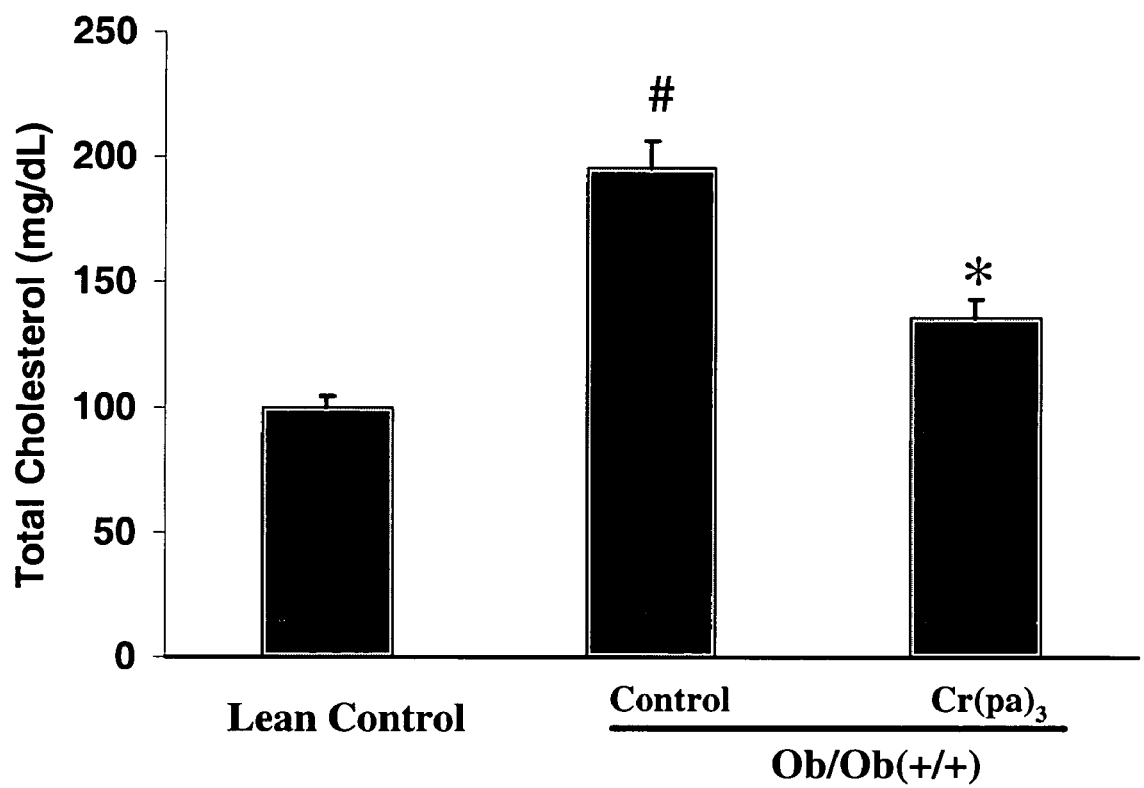
FIGS. 7A and 7B are graphical representations of the decrease in total plasma cholesterol levels (FIG. 7A) and total cholesterol compared to HDL (FIG. 7B) in obese mice treated with Cr(pa)$_3$.
Figure 7B:
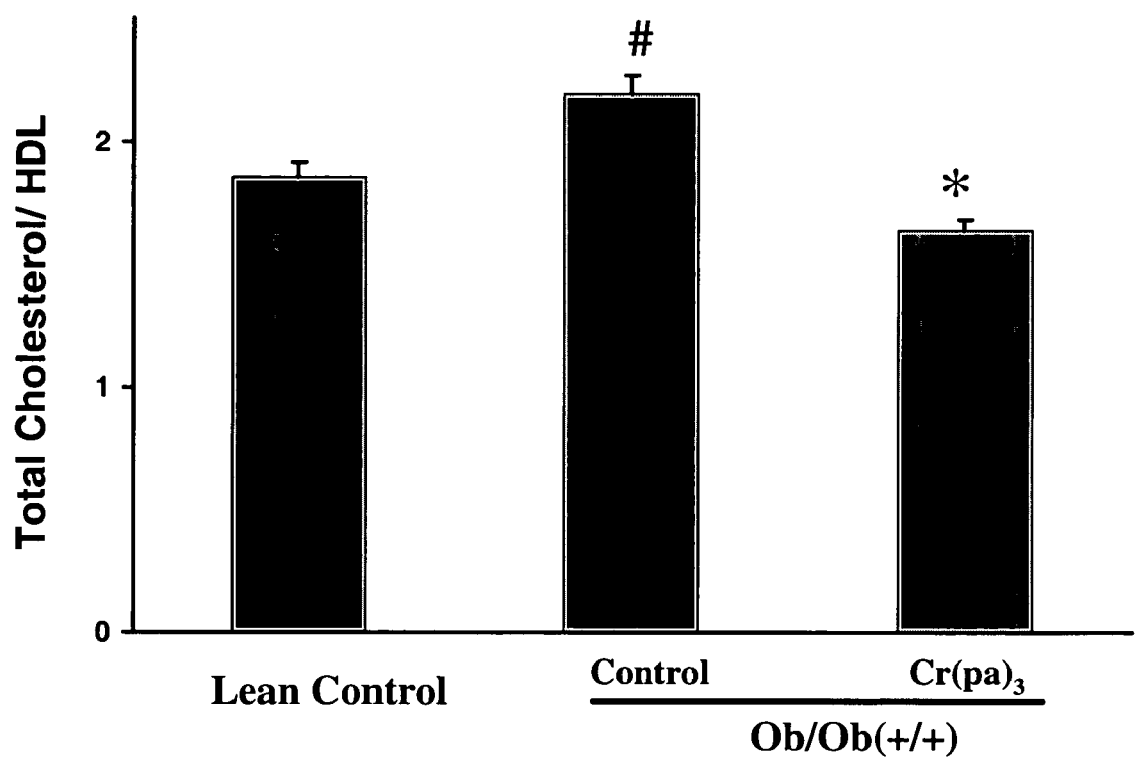

FIGS. 7A and 7B demonstrate that the treatment of obese mice with Cr(pa)$_3$ results a decrease in plasma cholesterol levels. Specifically, mice were treated with Cr(pa)$_3$ at 150 μg/kg/day for six weeks. Cholesterol levels were determined by using a kit from Equal Diagnostics (Exton, Pa.) following the manufacturer's protocol. Compared to lean mice, obese mice had elevated plasma cholesterol levels which was significantly attenuated following treatment with Cr (pa)$_3$.

EXAMPLE 2

Insulin resistance, concomitant with type II diabetes, obesity, hypertension, and other features of the metabolic syndrome is the major risk factor for cardio-vascular diseases and one of the leading causes of mortality and morbidity (DeFronzo, R. A. (2004) Med. Clin. North. Am., 88:787-835). Proper management of insulin resistance (with cardiovascular drugs as well as non-drug therapy such as exercise, caloric restriction) plays a pivotal role in reducing the risk for cardiovascular diseases. However, many drugs targeted for insulin resistance are often complicated with undesired effects which may compromise their ultimate clinical efficacy. Chromium is thought to play a key role in normal carbohydrate and lipid metabolism by potentiating the action of insulin (Vincent, J. B. (2004) Proc. Nutr. Soc., 63:41-47). Clinical trials have demonstrated that dietary chromium supplementation can lower blood glucose levels and improves lipid profile in diabetic patients (Morris et al. (2000) Diabet. Med., 17:684-685; Rabinovitz et al. (2004) Int. J. Vitam. Nutr. Res., 74:178-182).

Better bioavailability of low-molecular-weight (LMW)-organic chromium complexes and the identification that the biologically active form of chromium is a complex with an oligopeptide, prompted the design and evaluation of LMW-organic chromium complexes as therapeutic agents to counter the diminished effect of insulin in type-II diabetes (Yamamoto et al. (1987) Eur. J. Biochem., 165:627-631; Sun et al. (1999) J. Biol. Inorg. Chem., 4:838-845). Chromium complex of picolinic acid, the most popularly used dietary supplement has been shown to modulate intracellular pathways of glucose metabolism and improve comorbidities associated with insulin resistance in several animal and human studies (Anderson, R. A. (2000) Diabetes Metab., 26:22-27). However, recent reports that chromium picolinate may cause deleterious effects on DNA through generation of oxygen radicals, greatly limits its therapeutic utility (Hepburn et al. (2003) Proc. Natl. Acad. Sci. USA 100:3766-3771).

Chromium complexes of amino acids may be safer and efficacious alternatives to the commercially available chromium picolinate. As stated hereinabove, the chromium (D-phenylalanine)$_3$ [Cr(D-Phe)$_3$] complex improves insulin signal transduction and glucose uptake in cultured adipocytes. Cr(D-Phe)$_3$ also caused a marked improvement in glucose tolerance in obese mice and did not cause DNA-damage under physiological conditions. These studies suggest that chromium-amino acid complexes may serve as better alternatives to the chromium complexes that are currently used as dietary supplements.

Based on the aforementioned considerations the aim of the present study was to investigate the effect of chromium-amino acid complexes, particularly Cr(D-Phe)$_3$, on insulin-sensitivity, serum lipid profile and oxidative stress in a mouse model of type-II diabetes.

Materials

All antibodies used in this study were from Cell Signaling Technology Inc. (Beverly, Mass.). Micro BCA protein assay kit was from Pierce Chemical (Rockford, Ill.). Kits for triglyceride, total cholesterol and high density lipoprotein (HDL) were from Equal Diagnostics (Exton, Pa.). All other chemicals were from Sigma-Aldrich Chemical Co (St. Louis, Mo.).

Figure 8:
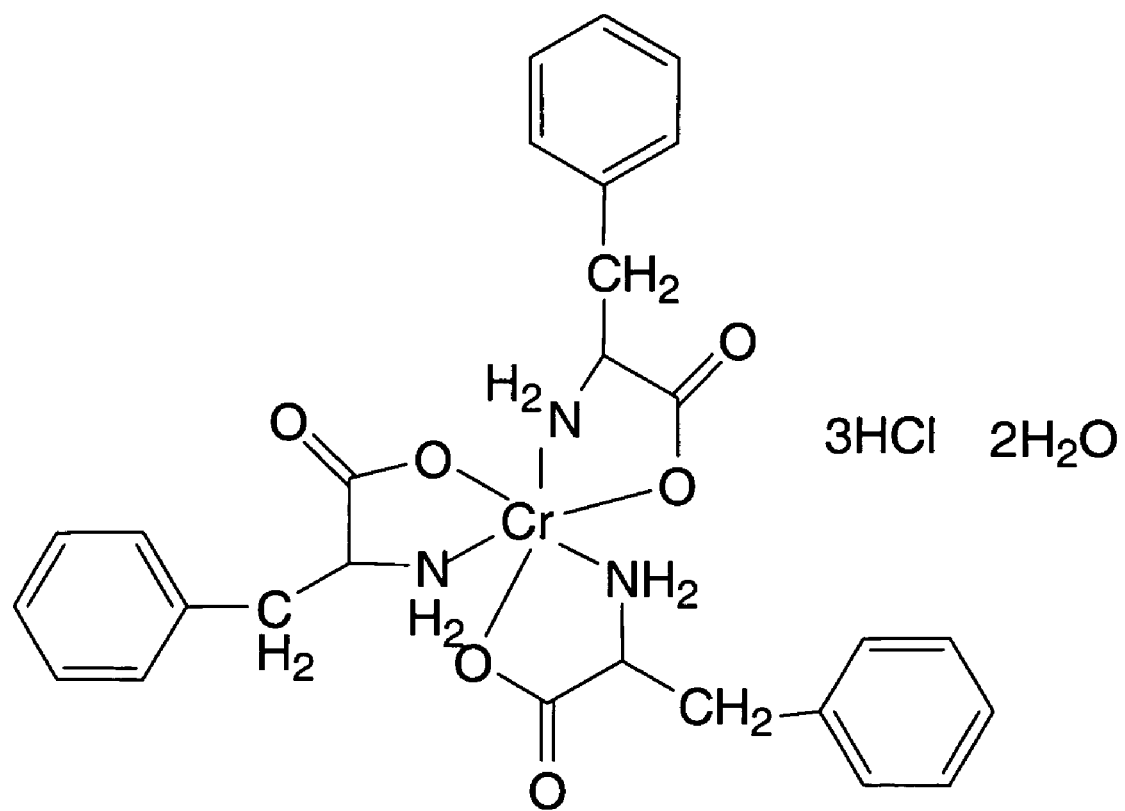
FIG. 8 is a structure for chromium(phenylalanine)$_3$ (Cr(pa)$_3$).

Cr(D-Phe)$_3$ was synthesized and characterized as described hereinabove. Briefly, aqueous solutions of CrCl$_3$.6H$_2$O (2.6 g; 10 mmol in 50 mL water) and D-phenylalanine (4.8 g, 30 mmol in 50 mL water) were mixed at 80° C. and refluxed for 4 hours. The homogeneous green reaction mixture was freeze-dried. The greenish-violet solid obtained was washed with acetone and dried in air oven. Based on the stoichiometry, elemental analysis and spectral studies, the product obtained is a complex containing chromium and phenylalanine in a ratio of 1:3 with the proposed structure as shown in FIG. 8.

All animal treatment procedures described in this study were approved by the Animal Care and Use Committee at University of Wyoming (Laramie, Wyo.). Homozygous B6.Vlep<ob>/J male mice purchased from the Jackson Laboratory (Bar Harbor, Me.) at age 5 weeks were divided randomly into two weight-matched groups, marked as ob/ob (+/+) control and ob/ob(+/+) treatment (n=12). Number and age-matched normal C57 mice were used as lean control. All animals were maintained on conventional laboratory diet under well-controlled conditions of temperature (22±2° C.), humidity (55±5%) and 12 hours/12 hours light-dark cycle and had ad libitum access to water and standard rodent chow. Cr(D-Phe)$_3$ was provided in the drinking water and, on the basis of water intake, was administered to provide an intake of about 150 µg/kg/day corresponding to about 10-15 µg elemental Cr/kg/day) for ob/ob(+/+) and lean treatment groups. One set of mice was used for the insulin-challenge test whereas the other set of mice, which did not receive insulin was fasted overnight and sacrificed by cerebral dislocation. The livers of these mice were frozen in liquid nitrogen immediately and stored at −80° C. until use. Blood was collected from the heart, and the serum was extracted by centrifuging the blood at 1000 g at 4° C. and stored at −80° C. Weights of body and other organs were measured with a standard laboratory scale.

At the end of the treatment schedule, mice were given intraperitoneal injections of insulin (1 U/kg body weight). Blood glucose levels were determined by the tail-clip method at different time points as described hereinabove.

Liver tissues lysates were subjected to Western blot analysis as described hereinabove using phospho specific antibodies against Akt. Blots were then stripped and re-probed with antibodies directed against antibodies directed at the total protein.

Serum levels of total cholesterol, high-density-lipoprotein (HDL) and triglycerides were measured using commercial kits (from Equal Diagnostics, Exton, Pa.) and SpectraMax 340PC$^{384}$ Microplate Reader System (Molecular Device, Sunnyvale, Calif.).

The end product of lipid-peroxidation, namely malondi-aldehyde (MDA), was estimated in the liver tissue homogenates by the colorimetric kit (Bioxytech LPO-586, Portland, Oreg.) using 1,1,3,3-tetra-ethoxypropane as a standard according to the manufacturer's specifications. This assay is based on the reaction of a chromogenic reagent N-methyl-2-phenylindole with MDA at 45° C. which yields a stable chromophore with absorbance maxima at 586 nm. Ability of Cr(D-Phe)$_3$ to inhibit in vitro lipid-peroxidation was assessed in rat-brain homogenates (10% w/v) by incubating Cr(D-Phe)$_3$ in the presence of hydrogen peroxide (1 mM) and ascorbic acid (1 mM) for 30 min at 37° C. followed by measuring MDA as described previously (Sreejayan et al. (1994) J. Pharm. Pharmacol., 46:1013-1016).

Protein-carbonyl content of total protein lysates from liver tissue was determined by calorimetrically estimating the product formed by the reaction of the carbonyls and 2,4-dinitrophenylhydrazine as described (Li et al. (2005) Aging Cell, 4:57-64).

Data are expressed as mean±SEM and statistically evaluated using Student's paired t-test using Sigma Plot statistical software (Jandel Scientific, San Rafael, Calif.). A 'p' value of less than 0.05 was considered to be statistically significant.

Results

The first set of experiments were aimed at investigating whether ingestion of oral Cr(D-Phe)$_3$ at a dose of 150 µg/kg/day for a six-week period altered the overall body-mass in genetically obese, leptin-deficient C57BL/6J ob/ob (+/+) mice. The mean base-line total body weight and weights of heart, liver, and kidney for the ob/ob(+/+) mice and their age-matched lean counterparts are shown in Table 1. Compared to the lean animals, obese animals had significantly higher absolute weights of body, heart and liver as anticipated. Treatment of obese mice with Cr(D-Phe)$_3$ 150 µg/kg/day for a six-week period did not alter any of these body-mass indices.

TABLE 1

Effect of Cr(D-Phe)$_3$-treatment on body and organ weight in obese animals.

| | Mouse group | | |
| --- | --- | --- | --- |
| | Lean | Ob/ob [Vehicle] | Ob/ob [Cr(D-Phe)3] |
| Body Weight (g) | 27.2 ± 1.0 | 53.4 ± 2.6* | 52.2 ± 1.6 |
| Heart Weight (mg) | 198 ± 20 | 304 ± 29* | 300 ± 30 |
| Heart/Weight (mg/g) | 7.3 ± 0.60 | 5.69 ± 0.35* | 5.75 ± 0.35 |
| Liver Weight (g) | 1.56 ± 0.17 | 3.45 ± 0.41* | 3.42 ± 0.23 |
| Liver/Body Weight (mg/g) | 57.6 ± 4.5 | 64.61 ± 4.81* | 65.52 ± 4.81 |
| Kidney Weight (mg) | 419 ± 35 | 421 ± 27 | 420 ± 20 |
| Kidney/Body Weight (mg/g) | 15.40 ± 0.85 | 7.88 ± 0.55* | 8.04 ± 0.55 |

The studies described hereinabove indicate that Cr(D-Phe)$_3$ improves insulin-signal transduction in cultured adipocytes. However, it is unclear whether this complex is capable of enhancing the functional effects of insulin in vivo. Therefore, the next set of experiments were aimed at investigating the effect of insulin-challenge on blood-glucose levels of ob/ob(+/+) mice treated with $Cr(D-Phe)_3$. Following oral treatment with $Cr(D-Phe)_3$ (150 μg/kg/day for 6 weeks) mice were challenged with an intraperitoneal injection of insulin (1 U/kg body weight). The time-course of blood-glucose levels following insulin-challenge in obese mice treated with $Cr(D-Phe)_3$ or vehicle is shown in FIG. 9. As expected, ob/ob(+/+) animals exhibited higher basal plasma glucose levels compared to their lean counterparts. Acute challenge with insulin caused a significant drop in the plasma glucose levels in both the obese and lean mice. However, in the chromium treated obese animals, the drop in glucose levels were significantly higher than that seen with untreated animals (115.3±18.0 mg/dL versus 175.8±43.2 mg/dL at 30 minutes post-challenge). In the lean mice, insulin-challenge failed to further lower the blood glucose level than that observed in the vehicle-treated group.

Akt has been identified as an important kinase, downstream of insulin receptor necessary for insulin activity (Katome et al. (2003) J. Biol. Chem., 278:28312-28323). As previously shown hereinabove, $Cr(D-Phe)_3$ can enhance the insulin-stimulated phosphorylation of Akt, in cultured adipocytes, suggesting that Akt may be a target protein for $Cr(D-Phe)_3$. An increase in Akt phosphorylation was also observed in individuals with type-II diabetes who supplemented their diet with chromium picolinate had increased activity of Akt (in the skeletal muscles) compared to those who were on placebo (Cefalu et. al., 18$^{th}$ International Diabetes Federation Congress, 2003). Based on these reports, the effects of oral $Cr(D-Phe)_3$-treatment on Akt phosphorylation in the liver homogenate of ob/ob(+/+) mice was studied. FIG. 10 shows the levels of phospho-Akt in the liver-homogenates, as assessed by Western blotting using a phospho-specific Akt antibody. Phospho-Akt levels in obese mice were significantly lower that observed in lean animals, suggesting that Akt may have a role to play in obesity and type II diabetes. However, oral treatment with $Cr(D-Phe)_3$ failed to significantly enhance the levels of phospho-Akt in the obese mice. Neither did the treatment alter the levels of the total Akt protein.

Recent reports have indicated that low-molecular weight organic chromium complexes can reduce fasting blood plasma low-density lipoprotein cholesterol, total cholesterol and triglycerides in diabetic rats (Clodfelder et al. (2005) J. Biol. Inorg. Chem., 10:119-130). Accordingly, the ability of $Cr(D-Phe)_3$ to alter the lipid profile in obese animals was tested. As shown in FIG. 11A, obese animals exhibited severe dyslipidemia compared to their lean counterparts as evidenced by significantly higher total serum cholesterol levels. Treatment with $Cr(D-Phe)_3$ caused a significant lowering of the total serum cholesterol levels (FIG. 11A). Serum levels of the beneficial HDL-cholesterol were higher in the obese animals compared to the lean mice (FIG. 11B). In contrast to serum cholesterol levels, treatment with $Cr(D-Phe)_3$ did not alter the levels of HDL-cholesterol. However, there was a significant decrease in the total serum cholesterol to HDL-cholesterol ratio in $Cr(D-Phe)_3$ animals: the ratios for the $Cr(D-Phe)_3$-treated and vehicle treated animals being 1.63±0.05 and 2.19±0.08, respectively. The difference in this ratio is thus attributable to the attenuation in serum cholesterol levels rather than any changes in the serum HDL levels.

Oxidant stress has been implicated as one of the causes and also an important consequence of diabetes and lipid dysfunctions (Scott et al. (2004) Ann. NY Acad. Sci., 1031:204-213). The levels of oxidant stress in liver homogenates as evidenced by the extent of lipid-peroxidation and protein carbonyl formation were significantly higher in obese, diabetic animals compared to lean animals. $Cr(D-Phe)_3$-treated animals had lower levels of these oxidative-stress markers compared to the untreated obese animals (FIGS. 12A and 12B). Besides in vivo lipid-peroxidation, $Cr(D-Phe)_3$ also inhibited in vitro lipid-peroxidation stimulated by hydrogen peroxide and ascorbate in rat-brain homogenates in a concentration-dependent manner (FIG. 13). These results suggest that the complex may possess a direct inhibitory effect on lipid-peroxidation.

Discussion $Cr(D-Phe)_3$, a novel chromium complex, enhances insulin signaling and glucose-uptake in cultured adipocytes. The present studies were designed to investigate the effects of this complex on insulin-sensitivity and plasma lipid profile in vivo. Here, it is shown that treatment of genetically-obese, leptin-deficient mice with $Cr(D-Phe)_3$ improves insulin-sensitivity and lowers total serum cholesterol. These results suggest that $Cr(D-Phe)_3$ may have beneficial effects in the prophylaxis and treatment of type II diabetes and obesity.

In addition to its effects on glucose, insulin, and lipid metabolism, chromium has been reported to increase lean body mass and decrease percentage body fat, which may lead to weight loss in humans (Anderson, R. A. (1998) J. Am. Coll. Nutr., 17:548-555). In the experiments described above, however, $Cr(D-Phe)_3$ did not alter the total body weight of obese animals indicating that the improvement in carbohydrate and lipid-metabolism did not translate into reduction of obesity in the particular model tested. This result is likely due to the short-term treatment schedule used in these experiments. Accordingly, long term treatment with $Cr(D-Phe)_3$ should prove effective in the treatment of obesity.

The insulin-stimulatory effect of $Cr(D-Phe)_3$ may be attributed to the ability of the complex to augment insulin-stimulated phosphorylation of key proteins such as the insulin-receptor beta and Akt in the insulin-signal-transduction cascade. A recently concluded clinical study suggests that chromium picolinate enhances the phosphorylation of Akt in skeletal muscles of diabetic patients (Cefalu et al., 18th International Diabetes Federation Congress, 2003). In the in vivo studies however, treatment with $Cr(D-Phe)_3$ failed to significantly enhance the levels of phospho-Akt in obese mice. Further, no changes in the phosphorylation of insulin-receptors (as assessed by reprobing the same blots with antibodies directed against the phosphorylated insulin receptor beta) were observed. The likely explanation for this lack of an observed effect is that basal phosphorylation levels were used as opposed to insulin-stimulated phosphorylation, which was the case with the in vitro experiments described hereinabove.

Several previous studies in experimental animals and human subjects have shown that chromium therapy may have beneficial effects in hyperlipidemic conditions (Rabinovitz et al. (2004) Int. J. Vitam. Nutr. Res., 74:178-182; Clodfelder et al. (2005) J. Biol. Inorg. Chem. 10:119-130; Cefalu et al. (2002) J. Nutr. 132: 1107-1114). The above results support this notion: $Cr(D-Phe)_3$-treatment lowered total serum cholesterol without altering HDL-cholesterol. Notably, the leptin-deficient ob/ob mice used in this study may not be an ideal model to study HDL owing to the fact that the basal HDL-cholesterol levels were significantly higher in these animals compared to the lean controls (FIG. 11B).

The picolinate ligand in the most popularly used chromium supplement, chromium picolinate, has been recently reported to shift the redox potential of chromium in the complex such that it can be reduced by biological reductants to generate hydroxyl radicals causing deleterious DNA mutations (Hepburn et al. (2003) Proc. Natl. Acad. Sci. USA, 100:3766-3771; Stearns et al. (1995) FASEB J. 9:1643-1648). In contrast to these findings, studies by Jain et al. (Biochem. Biophys. Res. Commun. (2001) 289:687-691) have shown that chromium chloride can inhibit oxidative stress induced by high glucose and hydrogen peroxide in cultured monocytes. Thus, the toxicity of chromium complex has been attributed to chromium picolinate but not chromium chloride indicating that the safety of chromium (III) is largely dependent on the ligand to which it is complexed (Bagchi et al. (2002) Toxicology 180:5-22). As shown hereinabove, chromium complexed with amino acid ligands fail to cause DNA nicking. The data also shows that $Cr(D-Phe)_3$ attenuates oxidant stress in vivo and in vitro. Thus, not only are chromium-amino acid complexes devoid of the DNA-damaging effects attributed to chromium picolinate, these complexes may also possess a direct antioxidant property. There are several reports that link the pathophysiology of diabetes and lipid-disorders to oxidative stress (Scott et al. (2004) Ann. NY Acad. Sci., 1031:204-213; Yu et al. (2005) Am. J. Med. Sci., 330:227-232). The ability of $Cr(D-Phe)_3$ to lower oxidative stress may thus add to its therapeutic value in treating diabetes and comorbid conditions.

In summary, it has been demonstrated that oral administration of $Cr(D-Phe)_3$ improves insulin-sensitivity, reduces total plasma cholesterol levels and attenuates hepatic oxidant stress in a mouse model of type-II diabetes and obesity. Taken together, these data suggest that $Cr(DPhe)_3$ may be of value in the therapy or prophylaxis of insulin-resistance and dyslipidemia associated with obesity.

EXAMPLE 3

Using the methods described hereinabove in Example 1, the effect of various chromium complexes on insulin-stimulated phosphorylation of Akt in 3T3-Adipocytes was studied. Particularly, the effects of chromium complexed with picolinate ($Cr(Pic)_3$), acetyl acetone ($Cr(AcAc)_3$), D-phenylalanine, L-phenylalanine, salicylate ($Cr(Sal)_3$), and chloride ($CrCl_3$) were determined. The results of the phosphorylation studies are provided in FIGS. 14A and 14B. Significantly, the administration of chromium complexes comprising D-phenylalanine or L-phenylalanine lead to the greatest amount of in vitro Akt phosphorylation suggesting that these chromium complexes are superior at promoting insulin signaling and glucose uptake.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A chromium (III) complex comprising D-amino acids.
2. The complex of claim 1, further comprising L-amino acids.
3. The complex of claim 1, wherein said amino acid is selected from the group consisting of phenylalanine, proline, cysteine, isoleucine, and methionine.
4. The complex of claim 1, wherein said amino acid is D-phenylalanine.
5. The complex of claim 4 of the formula:

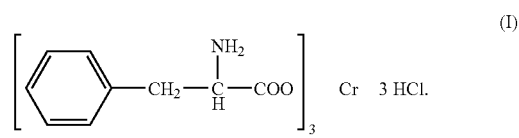

6. A composition comprising the complex of claim 1 and a pharmaceutically acceptable carrier.
7. The composition of claim 6, further comprising at least one agent for treating diabetes.
8. The composition of claim 6, further comprising at least one agent for lowering cholesterol.
9. A method of forming the complex of claim 1 comprising heating a mixture of a chromium (III) salt with three molar equivalents of said amino acids.
10. A method for the treatment of diabetes in a patient having diabetes, said method comprising administering an effective amount of the composition of claim 6.
11. A method for the treatment of insulin resistance syndrome in a patient having insulin resistance syndrome, said method comprising administering an effective amount of the composition of claim 6.
12. A method in preventing the onset of diabetes in a patient, said method comprising administering an effective amount of the composition of claim 6.
13. A method for decreasing plasma cholesterol levels in a patient in need thereof, said method comprising administering an effective amount of the composition of claim 6.
14. A chromium (III) complex comprising a derivative of D-phenylalanine.
15. The complex of claim 14, wherein said derivative of D-phenylalanine comprises substituents on the phenyl ring.
16. The complex of claim 14, wherein said derivative of D-phenylalanine is nateglinide.
17. A composition comprising a chromium (III) complex comprising amino acids, a pharmaceutically acceptable carrier, and at least one agent for lowering cholesterol.
18. A method for decreasing plasma cholesterol levels in a patient in need thereof, said method comprising administering an effective amount of the composition of claim 17.
19. The method of claim 18, wherein said amino acids are L- or D,L-amino acids.

* * * * *